(12) United States Patent
Doerner-Rieping et al.

(10) Patent No.: US 9,169,219 B2
(45) Date of Patent: Oct. 27, 2015

(54) HERBICIDALLY ACTIVE 4-NITRO-SUBSTITUTED N-(TETRAZOL-5-YL)-, N-(TRIAZOL-5-YL)-, AND N-(1,3,4-OXADIAZOL-2-YL)ARYL CARBOXYLIC ACID AMIDES

(71) Applicant: BAYER INTELLECTUAL PROPERTY GMBH, Monheim (DE)

(72) Inventors: Simon Doerner-Rieping, Neu-Anspach (DE); Ralf Braun, Ramberg (DE); Arnin Koehn, Klein-Winternheim (DE); Hartmut Ahrens, Egelsbach (DE); Stefan Lehr, Lyon (FR); Hansjoerg Dietrich, Liederbach (DE); Elmar Gatzweiler, Bad Nauheim (DE); Christopher Hugh Rosinger, Hofheim (DE); Dirk Schmutzler, Hattersheim (DE)

(73) Assignee: BAYER INTELLECTUAL PROPERTY GMBH, Monheim Am Rhein (DE)

( * ) Notice: Subject to any disclaimer, the term of this patent is extended or adjusted under 35 U.S.C. 154(b) by 0 days.

(21) Appl. No.: 14/379,553

(22) PCT Filed: Feb. 18, 2013

(86) PCT No.: PCT/EP2013/053200
§ 371 (c)(1),
(2) Date: Aug. 19, 2014

(87) PCT Pub. No.: WO2013/124245
PCT Pub. Date: Aug. 29, 2013

(65) Prior Publication Data
US 2015/0031537 A1    Jan. 29, 2015

(30) Foreign Application Priority Data

Feb. 21, 2012 (EP) ..................... 12156312

(51) Int. Cl.
| | | |
|---|---|---|
| *C07D 271/113* | (2006.01) | |
| *C07D 413/12* | (2006.01) | |
| *C07D 257/06* | (2006.01) | |
| *C07D 401/12* | (2006.01) | |
| *C07D 249/14* | (2006.01) | |
| *A01N 25/32* | (2006.01) | |
| *A01N 43/653* | (2006.01) | |
| *A01N 43/713* | (2006.01) | |
| *A01N 43/80* | (2006.01) | |
| *A01N 43/82* | (2006.01) | |

(52) U.S. Cl.
CPC ............. *C07D 249/14* (2013.01); *A01N 25/32* (2013.01); *A01N 43/653* (2013.01); *A01N 43/713* (2013.01); *A01N 43/80* (2013.01); *A01N 43/82* (2013.01); *C07D 257/06* (2013.01); *C07D 271/113* (2013.01); *C07D 401/12* (2013.01); *C07D 413/12* (2013.01)

(58) Field of Classification Search
CPC ............ C07D 249/14; C07D 271/113; C07D 413/12; C07D 257/06; C07D 401/12
See application file for complete search history.

(56) References Cited

U.S. PATENT DOCUMENTS

| 4,474,792 | A | 10/1984 | Erickson | |
| 8,481,749 | B2 * | 7/2013 | Braun et al. ............... | 548/265.4 |
| 2011/0152084 | A1 | 6/2011 | Koehn et al. | |
| 2012/0058892 | A1 * | 3/2012 | Braun et al. ................. | 504/103 |
| 2014/0080705 | A1 * | 3/2014 | Koehn et al. ................. | 504/105 |

FOREIGN PATENT DOCUMENTS

| EP | 268885 A1 | 1/2014 |
| JP | 2005314407 A | 11/2005 |
| WO | 0031066 A1 | 6/2000 |
| WO | 03027081 A1 | 4/2003 |
| WO | 2004080480 A1 | 9/2004 |
| WO | 2011035874 A1 | 3/2011 |
| WO | WO 2012028579 A1 * | 3/2012 |
| WO | WO 2012126932 A1 * | 9/2012 |
| WO | WO 2012130685 A1 * | 10/2012 |

OTHER PUBLICATIONS

Ladva et al. Indian Journal of Chemistry 1996, 35B, 1062-1066.*

(Continued)

*Primary Examiner* — Matthew Coughlin
(74) *Attorney, Agent, or Firm* — Miles & Stockbridge P.C.

(57) ABSTRACT

Herbicidally active 4-nitro-substituted N-(tetrazol-5-yl)-, N-(triazol-5-yl)- and N-(1,3,4-oxadiazol-2-yl)arylcarboxamides There are described 4-nitro-substituted N-(tetrazol-5-yl)-, N-(triazol-5-yl)- and N-(1,3,4-oxadiazol-2-yl)arylcarboxamides of the general formula (I) as herbicides.

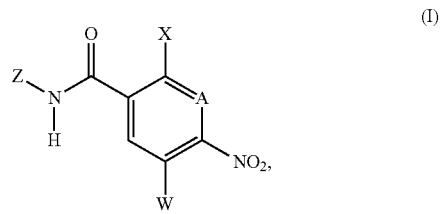

In this formula (I), X, Y and W are radicals such as hydrogen, organic radicals such as alkyl, and other radicals such as halogen. A is N and CY. Z is a tetrazolyl, triazolyl or oxadiazolyl radical

16 Claims, No Drawings

(56) References Cited

OTHER PUBLICATIONS

Wermuth, C.G. "Molecular Variations Based on Isosteric Replacements" in "The Practice of Medicinal Chemistry" 1996, Academic Press Limited, pp. 203-237.*

Patani et al. Chem. Rev. 1996, 96, 3147-3176.*

International Search Report received in corresponding PCT/EP2013/053200, mailed Apr. 8, 2013.

Zhurnal Organi-cheskoi Khimii (1965), 1(12), 2236-2244.

* cited by examiner

HERBICIDALLY ACTIVE 4-NITRO-SUBSTITUTED N-(TETRAZOL-5-YL)-, N-(TRIAZOL-5-YL)-, AND N-(1,3,4-OXADIAZOL-2-YL)ARYL CARBOXYLIC ACID AMIDES

CROSS REFERENCE TO RELATED APPLICATIONS

This application is a §371 National Stage Application of PCT/EP2013/053200, filed Feb. 18, 2013, which claims priority to EP 12156312.6, filed Feb. 21, 2012.

BACKGROUND

1. Field of the Invention

The invention relates to the technical field of herbicides, especially that of herbicides for selective control of broad-leaved weeds and weed grasses in crops of useful plants.

2. Description of Related Art

The compounds 4-nitro-N-(1H-tetrazol-5-yl)benzamide 3-chloro-4-nitro-N-(1H-tetrazol-5-yl)benzamide are known from WO 2004/080480 A1 and WO 2003/027081 A1 as chelating ligands for use in pharmaceutical insulin preparations. U.S. Pat. No. 4,474,792 describes the antiallergenic activity of 2-methoxy-4-nitro-N-(1H-tetrazol-5-yl)benzamide. Zhurnal Organicheskoi Khimii (1965), 1(12), 2236-2244 mentions the compound N-(1-methyl-1H-tetrazol-5-yl)-4-nitrobenzamide.

The herbicidal activity of the abovementioned compounds is not disclosed in these publications.

The compounds 2-chloro-N-(1-methyl-1H-tetrazol-5-yl)-4-nitro-benzamide and 2-chloro-4-nitro-N-(1-propyl-1H-tetrazol-5-yl)-benzamide are known under the CAS Nos. 638147-55-4 and 639050-55-8. A herbicidal activity of these two mentioned compounds is not disclosed.

The non-prior-published European patent application with earlier priority No. 10174893 discloses N-(tetrazol-5-yl)- and N-(triazol-5-yl)benzamides which bear a variety of substituents in position 4 of the phenyl ring, but no nitro group. The non-prior-published European patent application with earlier priority No. 11159115 describes N-(1,3,4-oxadiazol-2-yl)arylcarboxamides which bear a variety of substituents in position 4 of the phenyl ring, but no nitro group. However, the herbicidal activity and/or the crop plant compatibility of the compounds specified in these publications is not always adequate.

SUMMARY

It was an object of the present invention to provide further herbicidally active compounds.

It has now been found that N-(tetrazol-5-yl)-, N-(triazol-5-yl)- and N-(1,3,4-oxadiazol-2-yl)arylcarboxamides, which bear a nitro group in position 4 of the phenyl ring are particularly suitable as herbicides.

A subject matter of the present invention are therefore 4-nitro-substituted N-(tetrazol-5-yl)-, N-(triazol-5-yl)- and N-(1,3,4-oxadiazol-2-yl)arylcarbonamide of the formula (I) or their salts

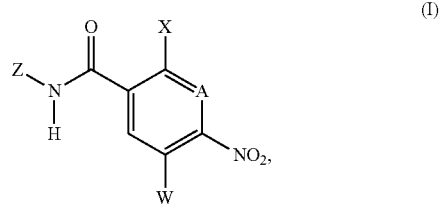

in which
Z is $Z^1$ or $Z^2$ $Z^1$:

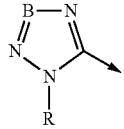

$Z^2$:

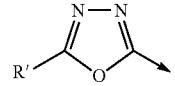

A is N or CY,
B is N or CH,
X is nitro, halogen, cyano, formyl, rhodano, $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_3$-$C_6)$-haloalkynyl, $(C_3$-$C_6)$-cycloalkyl, $(C_3$-$C_6)$-halocycloalkyl, $(C_3$-$C_6)$-cycloalkyl-$(C_1$-$C_6)$-alkyl, $(C_3$-$C_6)$-halocycloalkyl-$(C_1$-$C_6)$-alkyl, $R^1(O)C$, $R^1(R^1ON=)C$, $R^1O(O)C$, $(R^1)_2N(O)C$, $R^1O(R^1)N(O)C$, $R^1O$, $R^1(O)CO$, $(R^1)_2N(O)CO$, $R^2(O)_2SO$, $R^1O(O)CO$, $R^2(O)_nS$, $R^1O(O)_2S$, $(R^1)_2N(O)_2S$, $R^1(R^2)N$, $(R^1)_2N(O)C(R^1)N$, $R^1O(O)C(R^1)N$, $R^2(O)_2S(R^1)N$, $R^1(O)C(R^1)N$, $(R^5O)_2(O)P$, $(R^5O)_2(O)P$—$(C_1$-$C_6)$-alkyl, $R^2(O)_nS$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^1O(O)C$—$(C_1$-$C_6)$-alkyl, $R^1O(O)_2S$—$(C_1$-$C_6)$-alkyl, $(R^1)_2N(O)C$—$(C_1$-$C_6)$-alkyl, $(R^1)_2N(O)_2S$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, heteroaryl-$(C_1$-$C_6)$-alkyl or heterocyclyl-$(C_1$-$C_6)$-alkyl, where the two last-mentioned radicals are substituted in each case by s radicals from the group consisting of halogen, nitro, cyano, rhodano $(C_1$-$C_6)$-alkyl, $(C_1$-$C_6)$-haloalkyl, $(C_3$-$C_6)$-cycloalkyl, $(C_1$-$C_6)$-alkyl-$(O)_nS$, $(C_1$-$C_6)$-alkoxy and $(C_1$-$C_6)$-haloalkoxy, and where heterocyclyl bears n oxo groups,
Y is hydrogen, nitro, halogen, cyano, rhodano, $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_3$-$C_6)$-haloalkynyl, $(C_3$-$C_6)$-cycloalkyl, $(C_3$-$C_6)$-cycloalkenyl, $(C_3$-$C_6)$-halocycloalkyl, $(C_3$-$C_6)$-cycloalkyl-$(C_1$-$C_6)$-alkyl, $(C_3$-$C_6)$-halocycloalkyl-$(C_1$-$C_6)$-alkyl, $R^1(O)C$, $R^1O(O)C$, $R^1O(O)CO$, $R^1O(O)C(R^1)N$, $(R^1)_2N(O)C$, $(R^1)_2N(O)C(R^1)N$, $(R^1)_2N(O)CO$, $R^1O(R^1)N(O)C$, $R^2(O)_2S(R^1)N$, $R^1(O)C(R^1)N$, $R^1O$, $R^2(O)_2SO$, $(R^3)_2CNO$, $R^2(O)_nS$, $R^1O(O)_2S$, $(R^1)_2N(O)_2S$, $R^2(O)_2SO$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^1O(O)C$—$(C_1$-$C_6)$-alkyl, $NC$—$(C_1$-$C_6)$-alkyl, $R^1O(O)_2S$—$(C_1$-$C_6)$-alkyl, $(R^1)_2N(O)C$—$(C_1$-$C_6)$-alkyl, $(R^1)_2N(O)_2S$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $(R^1)_2N$, $(R^5O)_2(O)$ P, $(R^5O)_2(O)P$—$(C_1-C_6)$-alkyl, phenyl-$(C_1-C_6)$-alkyl, heteroaryl-$(C_1-C_6)$-alkyl, heterocyclyl-$(C_1-C_6)$-alkyl, phenyl, heteroaryl or heterocyclyl, where the last six radicals are substituted in each case by s radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkyl-$(O)_nS$, $(C_1-C_6)$-alkoxy, $(C_1-C_6)$-haloalkoxy, $(C_1-C_6)$-alkoxy-$(C_1-C_4)$-alkyl and cyanomethyl, and where heterocyclyl bears 0 to 2 oxo groups, W is hydrogen, halogen, nitro, cyano, rhodano, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_7)$-cycloalkyl, $(C_3-C_7)$-halocycloalkyl, $(C_1-C_6)$-alkoxy, $(C_1-C_6)$-haloalkoxy, $(C_1-C_6)$-alkyl-$(O)_nS$—, $(C_1-C_6)$-haloalkyl-$(O)_nS$—, $(C_1-C_6)$-alkoxy-$(C_1-C_4)$-alkyl, $(C_1-C_6)$-alkoxy-$(C_1-C_4)$-haloalkyl, $R^1(O)C$, $R^1(R^1ON=)C$, $R^1O(O)C$, $(R^1)_2N$, $R^1(O)C(R^1)N$ or $R^2(O)_2S(R^1)N$, R' is hydrogen, $(C_1-C_6)$-alkyl, $R^1O$—$(C_1-C_6)$-alkyl, $R^6H_2C$, $(C_3-C_7)$-cycloalkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $R^1O$, $R^1HN$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfanyl, methylsulfinyl, methylsulfonyl, or is heteroaryl, heterocyclyl, benzyl or phenyl, each of which is substituted by s radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkyl-$(O)_nS$, $(C_1-C_6)$-alkoxy, $(C_1-C_6)$-haloalkoxy, $(C_1-C_6)$-alkoxy-$(C_1-C_4)$-alkyl, where heterocyclyl bears n oxo groups, R is $(C_1-C_8)$-alkyl, $(C_1-C_8)$-haloalkyl, $(C_2-C_8)$-alkenyl, $(C_2-C_8)$-haloalkenyl or $(C_2-C_8)$-alkynyl, $(C_3-C_8)$-haloalkynyl, where these six abovementioned radicals are substituted in each case by s radicals from the group consisting of hydroxy, nitro, cyano, $(R^5)_3Si$, $(R^5O)_2(O)P$, $(C_1-C_6)$-alkyl-$(O)_nS$, $(C_1-C_6)$-haloalkyl-$(O)_nS$, $(C_1-C_6)$-alkoxy, $(C_1-C_6)$-haloalkoxy, $(R^3)_2N$, $R^3(O)C$, $R^3O(O)C$, $R^3(O)CO$, $R^3(O)C(R^3)N$, $R^4(O)_2S(R^3)N$, $(C_3-C_6)$-cycloalkyl-$(C_1-C_2)$-alkoxy, $(C_3-C_6)$-cycloalkyl, heteroaryl, heterocyclyl, phenyl, heteroaryl-Q, heterocyclyl-Q, phenyl-Q and Benzyl-Q, where the eight last-mentioned radicals are substituted in each case by s radicals from the group consisting of methyl, ethyl, methoxy, trifluoromethyl, cyano and halogen, and where heterocyclyl bears n oxo groups, or R is $(C_3-C_7)$-cycloalkyl, heteroaryl, heterocyclyl or phenyl, each of which is substituted by s radicals from the group consisting of halogen, nitro, cyano, $(C_1-C_6)$-Alkyl, $(C_1-C_6)$-haloalkyl, $(C_3-C_6)$-cycloalkyl, $(C_1-C_6)$-alkyl-$(O)_nS$, $(C_1-C_6)$-alkoxy, $(C_1-C_6)$-haloalkoxy and, $(C_1-C_6)$-alkoxy-$(C_1-C_4)$-alkyl, where heterocyclyl bears n oxo groups, Q is O, S or $(R^3)N$, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkoxy-$(C_1-C_6)$-alkyl, $(C_3-C_6)$-cycloalkyl-$(C_1-C_6)$-alkyl, phenyl, phenyl-$(C_1-C_6)$-alkyl, heteroaryl, heteroaryl-$(C_1-C_6)$-alkyl, heterocycl, heterocyclyl-$(C_1-C_6)$-alkyl, heteroaryl-O—$(C_1-C_6)$-alkyl, heterocyclyl-O—$(C_1-C_6)$-alkyl, heteroaryl-$(R^3)N$—$(C_1-C_6)$-alkyl or heterocyclyl-$(R^3)N$—$(C_1-C_6)$-alkyl, where the 21 last-mentioned radicals are substituted in each case by s radicals from the group consisting of cyano, halogen, nitro, rhodano, $R^3O$, $R^4(O)_nS$, $(R^3)_2N$, $R^3O(R^3)N$, $R^3(O)C$, $R^3(O)CO$, $R^4(O)CS$, $R^3(O)C(R^3)N$, $R^4(O)_2S(R^3)N$, $R^3(O)_2C$, $R^4S(O)C$, $(R^3)_2N(O)C$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkoxy-$(C_1-C_6)$-alkyl, $(C_3-C_6)$-cycloalkyl-$(C_1-C_6)$-alkyl, phenyl, phenyl-$(C_1-C_6)$-alkyl, heteroaryl, heteroaryl-$(C_1-C_6)$-alkyl, heterocycl, heterocyclyl-$(C_1-C_6)$-alkyl, heteroaryl-O—$(C_1-C_6)$-alkyl, heterocyclyl-O—$(C_1-C_6)$-alkyl, heteroaryl-$(R^3)N$—$(C_1-C_6)$-alkyl or heterocyclyl-$(R^3)N$—$(C_1-C_6)$-alkyl, where the 21 last-mentioned radicals are substituted in each case by s radicals from the group consisting of cyano, halogen, nitro, rhodano, $R^3O$, $R^4(O)_nS$, $(R^3)_2N$, $R^3O(R^3)N$, $R^3(O)C$, $R^3(O)CO$, $R^4(O)CS$, $R^3(O)C(R^3)N$, $R^4(O)_2S(R^3)N$, $R^3(O)_2C$, $R^4S(O)C$, $(R^3)_2N(O)C$ and $(C_1-C_4)$-alkoxy-$(C_2-C_6)$-alkoxycarbonyl, and where heterocyclyl bears n oxo groups, $R^3$ is hydrogen, $(C_1-C_6)$-alkyl, $(C_1-C_6)$-haloalkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^4$ is $(C_1-C_6)$-alkyl, $(C_1-C_6)$-haloalkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^5$ is $(C_1-C_4)$-alkyl, $R^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl, or is heteroaryl, heterocyclyl, in each case substituted by s radicals from the group methyl, ethyl, methoxy, trifluoromethyl and halogen, n is 0, 1 or 2, s is 0, 1, 2 or 3, with the proviso that the compounds 2-chloro-N-(1-methyl-1H-tetrazol-5-yl)-4-nitro-benzamide and 2-chloro-4-nitro-N-(1-propyl-1H-tetrazol-5-yl)-benzamide are not to be beard.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydro-2H-pyran-2-yl, tetrahydrofuran-2-yl, 1,4-dioxan-2-yl, 1,3-dioxolan-2-yl, dihydrofuranyl and oxetanyl.

Heteroaryl is an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned. This applies analogously to the formation of ring systems by various atoms and elements. At the same time, the scope of the claims shall exclude those compounds known to the person skilled in the art to be chemically unstable under standard conditions.

Depending on the nature and the attachment of the substituents, the compounds of the general formula (I) may be present as stereoisomers. When, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. Likewise, stereoisomers can be prepared selectively by employing stereoselective reactions using optically active starting materials and/or adjuvants. The invention also relates to all stereoisomers and mixtures thereof which are encompassed by the general formula (I) but not defined specifically. The invention also relates to all E/Z isomers and mixtures thereof which are encompassed by the general formula (I) but not defined specifically.

The compounds of the formula (I) are capable of forming salts. Salts may be formed by allowing a base to act on those compounds of the formula (I) which bear an acidic hydrogen atom, for example that of the Z(H)N(O)C amide group, or, in the event that $R^1$ has a COOH group or a sulfonamide group $NHSO_2$. Examples of suitable bases are organic amines such as trialkylamines, morpholine, piperidine, or pyridine, and the hydroxides, carbonates and hydrogencarbonates of ammonium, alkali metals or alkaline earth metals, in particular sodium hydroxide, potassium hydroxide, sodium carbonate, potassium carbonate, sodium hydrogencarbonate and potassium hydrogencarbonate. The salts are compounds in which the acidic hydrogen is replaced by an agriculturally suitable cation, for example metal salts, in particular alkali metal salts or alkaline earth metal salts, in particular sodium and potassium salts, or else ammonium salts, salts with organic amines or quaternary ammonium salts, for example with cations of the formula $[NR^aR^bR^cR^d]^+$, in which $R^a$ to $R^d$ in each case independently of one another are an organic radical, in particular alkyl, aryl, aralkyl or alkylaryl. Others which are suitable are alkylsulfonium and alkylsulfoxonium salts, such as $(C_1$-$C_4)$-trialkylsulfonium and $(C_1$-$C_4)$-trialkylsulfoxonium salts.

The compounds of the formula (I) can form salts by an addition reaction of a suitable inorganic or organic acid, such as, for example, mineral acids, such as, for example, HCl, HBr, $H_2SO_4$, $H_3PO_4$ or $HNO_3$, or organic acids, for example carboxylic acids, such as formic acid, acetic acid, propionic acid, oxalic acid, lactic acid or salicylic acid or sulfonic acids such as, for example, p-toluenesulfonic acid, with a basic group such as, for example, amino, alkylamino, dialkylamino, piperidino, morpholino or pyridine. In such a case, the salts will comprise the conjugated base of the acid as the anion.

Preference is given to compounds of the general formula (I) in which
Z is $Z^1$ or $Z^2$ $Z^1$:

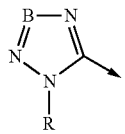

$Z^2$:

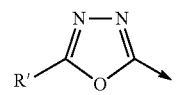

A is N or CY,
B is N or CH,
X is nitro, halogen, cyano, formyl, $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_3$-$C_6)$-cycloalkyl, $(C_3$-$C_6)$-halocycloalkyl, $(C_3$-$C_6)$-cycloalkyl-$(C_1$-$C_6)$-alkyl, $R^1(O)C$, $R^1O(O)C$, $(R^1)_2N(O)C$, $R^1O$, $R^1(O)CO$, $(R^1)_2N(O)CO$, $R^1O(O)CO$, $R^2(O)_nS$, $(R^1)_2N(O)_2S$, $R^1(R^2)N$, $R^2(O)_2S(R^1)N$, $R^1(O)C(R^1)N$, $R^2(O)_nS$—$(C_1$-$C_6)$-alkyl, $R^1O$—$(C_1$-$C_6)$-alkyl, $R^1(O)CO$—$(C_1$-$C_6)$-alkyl, $R^1O(O)C$—$(C_1$-$C_6)$-alkyl, $(R^1)_2N(O)C$—$(C_1$-$C_6)$-alkyl, $(R^1)_2N(O)_2S$—$(C_1$-$C_6)$-alkyl, $R^2(O)_2S(R^1)N$—$(C_1$-$C_6)$-alkyl, heteroaryl-$(C_1$-$C_6)$-alkyl or heterocyclyl-$(C_1$-$C_6)$-alkyl, where the two last-mentioned radicals are substituted in each case by s radicals from the group consisting of halogen, nitro, cyano, $(C_1$-$C_6)$-alkyl, $(C_1$-$C_6)$-haloalkyl, $(C_3$-$C_6)$-cycloalkyl, $(C_1$-$C_6)$-alkyl-$(O)_nS$, $(C_1$-$C_6)$-alkoxy and $(C_1$-$C_6)$-haloalkoxy, and where heterocyclyl bears n oxo groups,
Y is hydrogen, nitro, halogen, cyano, $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_3$-$C_6)$-haloalkynyl, $(C_3$-$C_6)$-cycloalkyl, $(C_3$-$C_6)$-cycloalkenyl, $(C_3$-$C_6)$-halocycloalkyl, $(C_3$-$C_6)$-cycloalkyl-$(C_1$-$C_6)$-alkyl, $(C_3$-$C_6)$-halocycloalkyl-$(C_1$-$C_6)$-alkyl, $R^1(O)C$, $R^1O(O)C$, $R^1O(O)CO$, $R^1O(O)C(R^1)N$, $(R^1)_2N(O)C$, $(R^1)_2N(O)C(R^1)N$, $(R^1)_2N(O)CO$, $R^1O(R^1)N(O)C$, $R^2(O)_2S(R^1)N$, $R^1(O)C(R^1)N$, $R^1O$, $R^2(O)_2SO$, $R^2(O)_nS$, $R^1O(O)_2S$, $(R^1)_2N(O)_2S$, $R^1O$—$(C_1$-$C_6)$-alkyl, $R^1(O)CO$—$(C_1$-$C_6)$-alkyl, $R^1O(O)C$—$(C_1$-$C_6)$-alkyl, NC—$(C_1$-$C_6)$-alkyl, $(R^1)_2N(O)C$—$(C_1$-$C_6)$-alkyl, $(R^1)_2N(O)_2S$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $(R^1)_2N$, phenyl-$(C_1$-$C_6)$-alkyl, heteroaryl-$(C_1$-$C_6)$-alkyl, heterocyclyl-$(C_1$-$C_6)$-alkyl, heteroaryl or heterocyclyl, where the last five radicals are substituted in each case by s radicals from the group halogen, nitro, cyano, $(C_1$-$C_6)$-alkyl, $(C_1$-$C_6)$-haloalkyl, $(C_3$-$C_6)$-cycloalkyl, $(C_1$-$C_6)$-alkyl-$(O)_nS$, $(C_1$-$C_6)$-alkoxy, $(C_1$-$C_6)$-haloalkoxy, $(C_1$-$C_6)$-alkoxy-$(C_1$-$C_4)$-alkyl and cyanomethyl, and where heterocyclyl bears 0 to 2 oxo groups,
W is hydrogen, halogen, nitro, cyano, $(C_1$-$C_6)$-alkyl, $(C_1$-$C_6)$-haloalkyl, $(C_3$-$C_7)$-cycloalkyl, $(C_1$-$C_6)$-alkoxy, $(C_1$-$C_6)$-alkyl-$(O)_nS$—, $R^1O(O)C$, $(R^1)_2N$, $R^1(O)C(R^1)N$ or $R^2(O)_2S(R^1)N$,
R' is hydrogen, $(C_1$-$C_6)$-alkyl, $R^1O$—$(C_1$-$C_6)$-alkyl, $R^6H_2C$, $(C_3$-$C_7)$-cycloalkyl, $(C_1$-$C_6)$-haloalkyl, $R^1O$, $R^1HN$, methoxycarbonyl, ethoxycarbonyl, methoxycarbonylmethyl, ethoxycarbonylmethyl, methylcarbonyl, acetylamino or methylsulfonyl, R is $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl or $(C_3-C_8)$-haloalkynyl, where these six abovementioned radicals are substituted in each case by s radicals from the group consisting of $(C_1-C_6)$-alkyl-$(O)_n$S, $(C_1-C_6)$-alkoxy, $(C_1-C_6)$-haloalkoxy, $(R^3)_2N$, $R^3(O)C$, $R^3O(O)C$, $R^3(O)CO$, $R^3(O)C(R^3)N$, $R^4(O)_2S(R^3)N$, $(C_3-C_6)$-cycloalkyl, heteroaryl, heterocyclyl and phenyl, where the four last-mentioned radicals are substituted in each case by s radicals from the group consisting of methyl, ethyl, methoxy, trifluoromethyl, cyano and halogen, and where heterocyclyl bears n oxo groups, or R is $(C_3-C_7)$-cycloalkyl, heteroaryl, heterocyclyl or phenyl, each of which is substituted by s radicals from the group consisting of halogen, $(C_1-C_6)$-alkyl, $(C_1-C_6)$-haloalkyl, $(C_1-C_6)$-alkyl-$(O)_n$S, $(C_1-C_6)$-alkoxy and $(C_1-C_6)$-haloalkoxy, where heterocyclyl bears n oxo groups, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkoxy-$(C_1-C_6)$-alkyl, $(C_3-C_6)$-cycloalkyl-$(C_1-C_6)$-alkyl, phenyl, phenyl-$(C_1-C_6)$-alkyl, heteroaryl, heteroaryl-$(C_1-C_6)$-alkyl, heterocycl or heterocyclyl-$(C_1-C_6)$-alkyl, where the 17 last-mentioned radicals are substituted in each case by s radicals from the group consisting of cyano, halogen, nitro, $R^3O$, $R^4(O)_nS$, $(R^3)_2N$, $R^3(O)CO$, $R^3(O)_2C$ and $(R^3)_2N(O)C$, and where heterocyclyl bears n oxo groups, $R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkoxy-$(C_1-C_6)$-alkyl, $(C_3-C_6)$-cycloalkyl-$(C_1-C_6)$-alkyl, phenyl, phenyl-$(C_1-C_6)$-alkyl, heteroaryl, heteroaryl-$(C_1-C_6)$-alkyl, heterocycl or heterocyclyl-$(C_1-C_6)$-alkyl, where the 17 last-mentioned radicals are substituted in each case by s radicals from the group consisting of cyano, halogen, nitro, $R^3O$, $R^4(O)_nS$, $(R^3)_2N$, $R^3(O)CO$, $R^3(O)_2C$ and $(R^3)_2N(O)C$, and where heterocyclyl bears n oxo groups, $R^3$ is hydrogen, $(C_1-C_6)$-alkyl, $(C_1-C_6)$-haloalkyl or $(C_3-C_6)$-cycloalkyl, $R^4$ is $(C_1-C_6)$-alkyl, $(C_1-C_6)$-haloalkyl or $(C_3-C_6)$-cycloalkyl, $R^6$ is acetoxy, acetamido, methoxycarbonyl, ethoxycarbonyl, $(C_1-C_6)$-alkoxy or $(C_3-C_6)$-cycloalkyl, n is 0, 1 or 2, s is 0, 1, 2 or 3, with the proviso that the compounds 2-chloro-N-(1-methyl-1H-tetrazol-5-yl)-4-nitro-benzamide and 2-chloro-4-nitro-N-(1-propyl-1H-tetrazol-5-yl)-benzamide are not to be included.

Particular preference is given to compounds of the general formula (I) in which
Z is $Z^1$ or $Z^2$ $Z^1$:

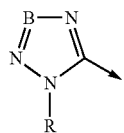

$Z^2$:

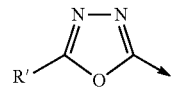

A is CY,

B is N or CH,

X is nitro, halogen, cyano, methyl, ethyl, n-propyl, isopropyl, trifluoromethyl, difluoromethyl, pentafluoroethyl, cyclopropyl, cyclopropylmethyloxy, methoxy, ethoxy, methylsulfanyl, methylsulfinyl, methylsulfonyl, methoxymethyl, ethoxymethyl, 2-methoxyethoxymethyl, methylsulfanylmethyl, methylsulfinylmethyl or methylsulfonylmethyl, Y is hydrogen, nitro, halogen, cyano, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-cycloalkyl, $(C_3-C_6)$-cycloalkyl-$(C_1-C_6)$-alkyl, $R^1(O)C$, $R^1O(O)C$, $R^1O$, $R^2(O)_nS$, $R^1O$—$(C_1-C_6)$-alkyl, NC—$(C_1-C_6)$-alkyl, $(R^1)_2N$, heteroaryl-$(C_1-C_6)$-alkyl, heterocyclyl-$(C_1-C_6)$-alkyl, heteroaryl or heterocyclyl, where the last four radicals are substituted in each case by s radicals from the group halogen, nitro, cyano, methyl, trifluoromethyl, methoxy and methylsulfonyl, and where heterocyclyl bears n oxo groups, W is hydrogen, chlorine, methyl, R' is methyl, ethyl, n-propyl or methoxymethyl, R is methyl, ethyl, n-propyl, prop-2-en-1-yl, 2-methoxyethyl, 2-ethoxyethyl or 2-(2-methoxyethoxy)ethyl, $R^1$ is hydrogen, methyl, ethyl, n-propyl, isopropyl, prop-2-enyl, prop-2-inyl, trifluoromethyl, difluoromethyl, fluoromethyl, 2,2,2-trifluoroethyl, 2,2-difluoroethyl, 2-fluoroethyl, 2-chloroethyl, cyclopropyl, 2-methoxyethyl, 2-ethoxyethyl, 3-methoxypropyl, 3-ethoxypropyl, cyclopropylmethyl, 2-(trifluoromethoxy)ethyl, 3-(trifluoromethoxy)propyl, 2-(trifluoromethylsulfanyl)ethyl, 2-(trifluoromethylsulfyny)lethyl, 2-(trifluoromethylsulfonyl)ethyl, 3-(trifluoromethylsulfanyl)propyl, 3-(trifluoromethylsulfinyl)propyl, 3-(trifluoromethylsulfonyl)propyl, N,N-dimethylaminocarbonylmethyl, 3-(1H-tetrazol-1-yl)propyl, 3-(1H-tetrazol-2-yl)propyl, tetrahydrofuran-2-yl-methyl, 1,4-dioxan-2-ylmethyl, 1,3-dioxolan-2-ylmethyl, 2-methylsulfonylaminoethyl $R^2$ is methyl, ethyl, n-propyl, isopropyl, prop-2-enyl, prop-2-inyl, trifluoromethyl, difluoromethyl, fluoromethyl, 2,2,2-trifluoroethyl, 2,2-difluoroethyl, 2-fluoroethyl, 2-chloroethyl, cyclopropyl, 2-methoxyethyl, 2-ethoxyethyl, 3-methoxypropyl, 3-ethoxypropyl, cyclopropylmethyl, 2-(trifluoromethoxy)ethyl, 3-(trifluoromethoxy)propyl, 2-(trifluoromethylsulfanyl)ethyl, 2-(trifluoromethylsulfiny)lethyl, 2-(trifluoromethylsulfonyl)ethyl, 3-(trifluoromethylsulfanyl)propyl, 3-(trifluoromethylsulfinyl)propyl, 3-(trifluoromethylsulfonyl)propyl, N,N-dimethylaminocarbonylmethyl, 3-(1H-tetrazol-1-yl)propyl, 3-(1H-tetrazol-2-yl)propyl, tetrahydrofuran-2-yl-methyl, 1,4-dioxan-2-ylmethyl, 1,3-dioxolan-2-ylmethyl, 2-methylsulfonylaminoethyl n is 0, 1 or 2, s is 0, 1, 2 or 3, with the proviso that the compounds 2-chloro-N-(1-methyl-1H-tetrazol-5-yl)-4-nitro-benzamide and 2-chloro-4-nitro-N-(1-propyl-1H-tetrazol-5-yl)-benzamide are not to be included.

In all the formulae specified hereinafter, the substituents and symbols have the same meaning as in formula (I), unless defined differently.

Compounds according to the invention can be prepared for example by the method shown in scheme 1 by the base-catalyzed reaction of a pyridinecarboyl chloride (II) with heterocyclic amines Z—NH₂ (III):

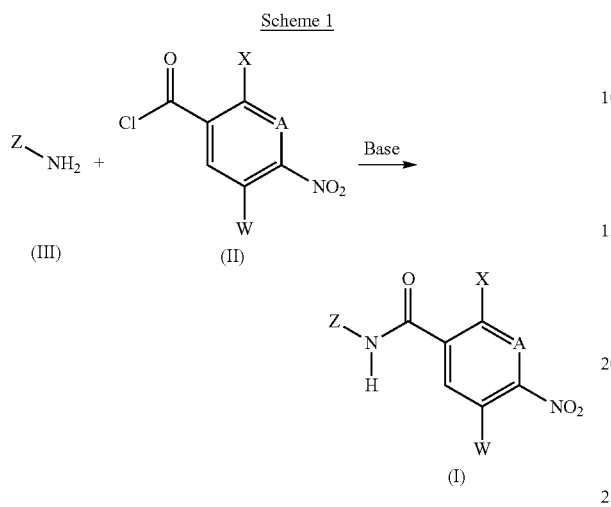

The benzoyl chlorides of the formula (II), or the benzoic acids on which they are based, are known in principle and can be prepared for example by the methods described in JP63122673, WO 99/54328 A1, WO 97/46530 A1 and WO 90/05712 A1.

Compounds according to the invention can also be prepared by the method shown in scheme 2 by reaction of a benzoic acid of the formula (IV) with a heterocyclic amine Z—NH₂ (III):

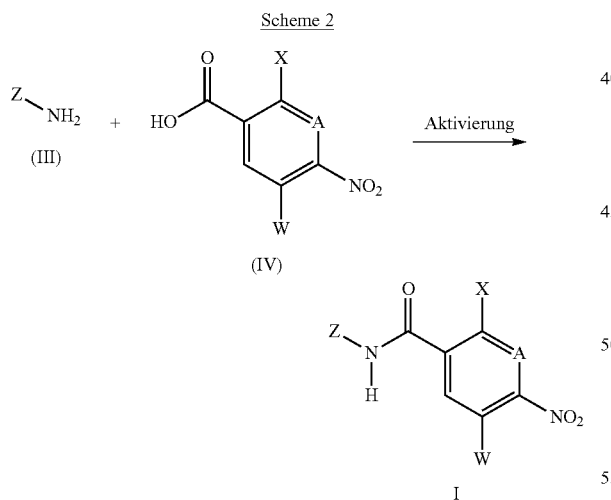

Dehydrating reagents such as, for example, 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) and the like, which are conventionally employed in amidation reactions, may be employed for the activation.

Compounds according to the invention in which Z is $Z^1$ can also be prepared by the method shown in scheme 3 by reaction of an N-(1H-1,2,4-triazol-5-yl)benzamide, N-(1H-tetrazol-5-yl)benzamide, N-(1H-1,2,4-triazol-5-yl)nicotinamide or N-(1H-tetrazol-5-yl)nicotinamide:

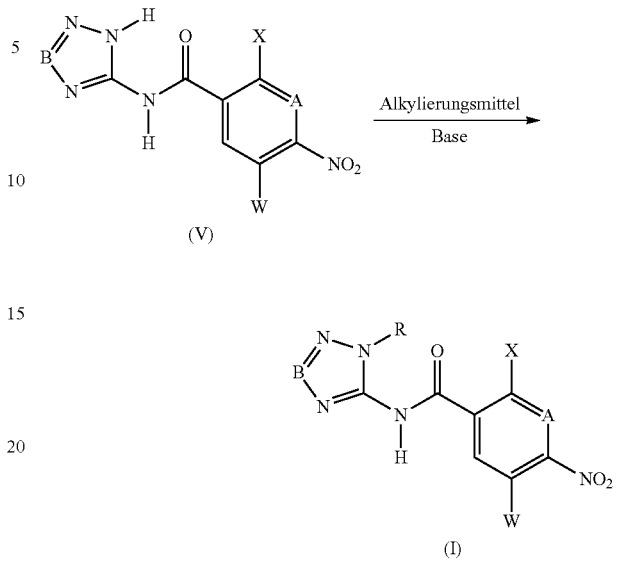

Alkylating agents such as, for example, alkyl halides, alkyl sulfonates or dialkyl sulfates in the presence of a base, may be employed for this reaction which is shown in scheme 3.

Compounds according to the invention in which Z is $Z^2$ can also be prepared by the method shown in scheme 4 by cyclization of a compound of the formula (VI):

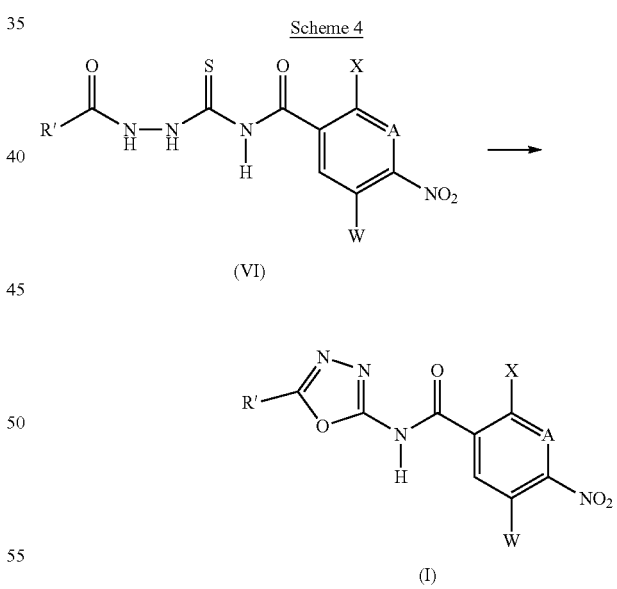

The cyclization can be carried out according to the methods described in Synth. Commun. 31 (12), 1907-1912 (2001) or in Indian J. Chem., Section B: Organic Chemistry Including Medicinal Chemistry; vol. 43 (10), 2170-2174 (2004). The compounds of the formula (VI), which can be employed for the cyclization, can be prepared as shown in scheme 5 by reaction of an acyl isocyanate of the formula (VIII) with a hydrazide of the formula (VII) in accordance with the method described in *Synth. Commun.* 25(12), 1885-1892 (1995).

Scheme 5

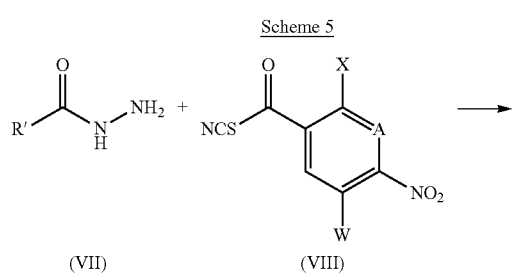

Scheme 8

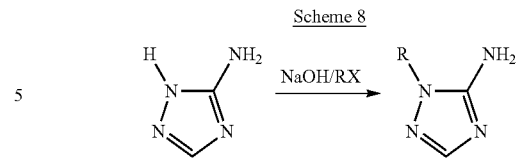

5-amino-1-R-triazoles can, for example, also be synthesized as described in Chemische Berichte (1964), 97(2), 396-404:

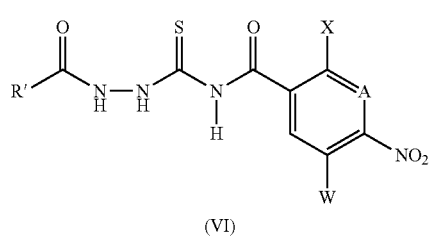

Scheme 9

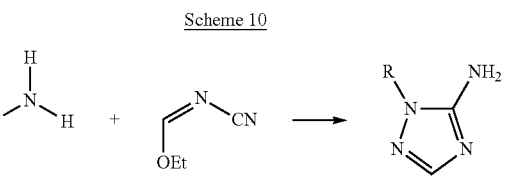

5-amino-1-R-triazoles can, for example, also be synthesized as described in Angewandte Chemie (1963), 75, 918:

The heterocyclic amines Z—NH$_2$ of the formula (III), in which Z is Z$^1$ and B is N, are either commercially available or can be prepared analogously to methods known from the literature as shown in scheme 6 and scheme 7. For example, 5-amino-1-R-tetrazoles can be prepared by the method described in Journal of the American Chemical Society (1954), 76, 923-924, starting from 5-amino-1H-tetrazole:

Scheme 10

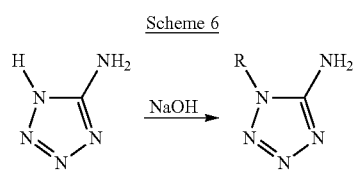

Here, R is for example an alkyl radical.

It may be expedient to change the order of the reaction steps. For instance, benzoic acids bearing a sulfoxide cannot be converted directly to their acid chlorides. One option here is first to prepare the amide at the thioether level and then to oxidize the thioether to give the sulfoxide.

Scheme 6

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

As an alternative, 5-amino-1-R-tetrazoles can also be synthesized for example as described in Journal of the American Chemical Society (1954) 76, 88-89:

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

Scheme 7

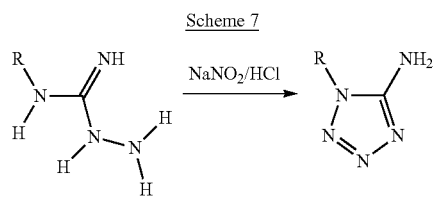

The heterocyclic amines Z—NH$_2$ of the formula (III), in which Z is Z$^1$ and B is CH, are either commercially available or can be prepared analogously to methods known from the literature as shown in schemes 8-10. For example, 5-amino-1-R-triazoles can be prepared by the method described in Zeitschrift für Chemie (1990), 30(12), 436-437, starting from 5-amino-1H-triazole:

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a series of protocols which are known from the literature which, again, can be accomplished in a manual or automated manner. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), collectively referred to hereinafter as "inventive compounds", have excellent herbicidal efficacy against a broad spectrum of economically important monocotyledonous and dicotyledonous annual weed plants. The active ingredients also have good control over perennial weed plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species:

Monocotyledonous weed plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the emergence of the weed seedlings is either prevented completely, or the weeds grow until they have reached the cotyledon stage, but then growth stops and, ultimately, after three to four weeks have elapsed, they die completely.

If the active ingredients are applied post-emergence to the green parts of the plants, there is likewise stoppage of growth after the treatment, and the weed plants remain at the growth stage of the time of application, or they die completely after a certain time, such that competition by the weeds, which is harmful to the crop plants, is thus eliminated very early and in a lasting manner.

Although the compounds according to the invention have an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, will, depending on the structure of the respective compound according to the invention and its application rate, be damaged to a negligible extent only, or not at all. For these reasons, the present compounds are highly suited to the selective control of undesired plant growth in crops of plants, such as stands of agricultural crops or ornamentals.

In addition, the compounds according to the invention (depending on their particular structure and the application rate deployed) have outstanding growth-regulating properties in crop plants. They engage in the plants' metabolism in a regulatory manner and can therefore be employed for influencing, in a targeted manner, plant constituents and for facilitating harvesting, such as, for example, by triggering desiccation and stunted growth. Moreover, they are also suitable for generally controlling and inhibiting undesired vegetative growth without destroying the plants in the process. Inhibiting vegetative growth plays a major role for many monocotyledonous and dicotyledonous crops, since, for example, this can reduce or completely prevent lodging.

By virtue of their herbicidal and plant-growth-regulatory properties, the active substances can also be employed for controlling harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferred, with respect to transgenic crops, to use the compounds according to the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Preference is given to the use of the compounds according to the invention or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the compounds according to the invention can be employed as herbicides in crops of useful plants which are resistant, or have been made to be resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

recombinant modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylureas (EP-A-0257993, U.S. Pat. No. 5,013,659)

transgenic crop plants, for example cotton, with the ability to produce *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel plant constituents or secondary metabolites, for example novel phytoalexins, which bring about an increased disease resistance (EPA 309862, EPA0464461)

genetically modified plants with reduced photorespiration, which feature higher yields and higher stress tolerance (EPA 0305398).

transgenic crop plants which produce pharmaceutically or diagnostically important proteins ("molecular pharming"), transgenic crop plants which are distinguished by higher yields or better quality transgenic crop plants which are distinguished by a combination, for example of the abovementioned novel properties ("gene stacking")

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of standard methods. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to intact plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or which express heterologous (=foreign) genes or gene sequences.

Preferably, the inventive compounds can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the inventive active ingredients in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds as herbicides for control of weed plants in transgenic crop plants.

The inventive compounds can be applied in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways, according to the biological and/or physicochemical parameters required. Examples of possible formulations include: Wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil-or-water-based dispersions, oil-miscible solutions, capsule suspensions (CS), dustable powders (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and further additives, are likewise known and described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Engineering], volume 7, C. Hanser Verlag Munich, 4th ed. 1986.

Based on these formulations, it is also possible to produce combinations with other pesticidally active compounds, such as, for example, insecticides, acaricides, herbicides, fungicides, and with safeners, fertilizers and/or growth regulators, for example in the form of a readymix or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To prepare the wettable powders, the herbicidally active substances are ground finely, for example in customary apparatus such as hammer mills, blower mills and air-jet mills, and simultaneously or subsequently mixed with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active compound with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active substance onto adsorptive granular inert material or by applying active substance concentrates to the surface of carriers, such as sand, kaolinites or granular inert material, by means of adhesives, for example polyvinyl alcohol, sodium polyacrylates or mineral oils. Suitable active ingredients can also be granulated in the manner customary for the production of fertilizer granules—if desired as a mixture with fertilizers.

Water-dispersible granules are prepared generally by the customary processes such as spray-drying, fluidized-bed granulation, pan granulation, mixing with high-speed mixers, and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active substance concentration is, for example, approximately 10 to 90% by weight, the remainder to 100% by weight consisting of customary formulation components. In the case of emulsifiable concentrates, the active substance concentration can be from about 1 to 90, preferably 5 to 80% by weight. Formulations in the form of dusts comprise 1 to 30% by weight of active ingredient, preferably usually 5 to 20% by weight of active ingredient; sprayable solutions contain about 0.05 to 80, preferably 2 to 50, % by weight of active ingredient. In the case of water-dispersible granules, the active ingredient content depends partly on whether the active compound is present in liquid or solid form and on which granulation assistants, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2009 and literature cited therein. Examples of known herbicides or plant growth regulators which can be combined with the inventive compounds include the active ingredients which follow (the compounds are designated either by the "common name" according to the International Organization for Standardization (ISO) or by the chemical name or by the code number) and always encompass all use forms, such as acids, salts, esters and isomers, such as stereoisomers and optical isomers. One administration form or else, in some cases, more than one administration form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryne, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulacsodium, dimefuron, dimepiperate, dimethachlor, dimethametryne, dimethenamid, dimethenamid-P, dimethipin, dimetrasulfuron, dinitramine, dinoseb, dinoterb, diphenamid, dipropetryne, diquat, diquat dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]-phenyl]-ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H, 3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl)-O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)-ethyl(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl] methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryne, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryne, SN-106279, i.e. methyl (2R)-2-({7-[2-chloro-4-(trifluoromethyl)phenoxy]-2-naphthyl}oxy)propanoate, sulcotrione, sulfo-allate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl-5-[2-chloro-4-(trifluoromethyl)phenoxy]-2-nitrobenzoate, SYP-300, i.e. 1-[7-fluoro-3-oxo-4-(prop-2-in-1-yl)-3,4-dihydro-2H-1,4-benzoxazine-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

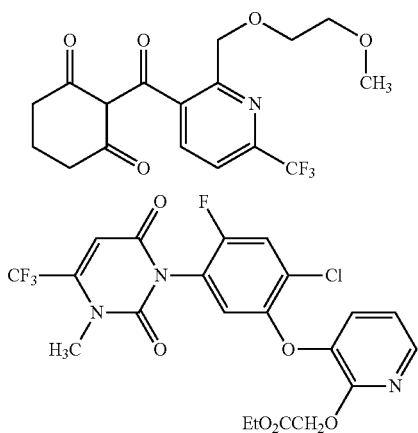

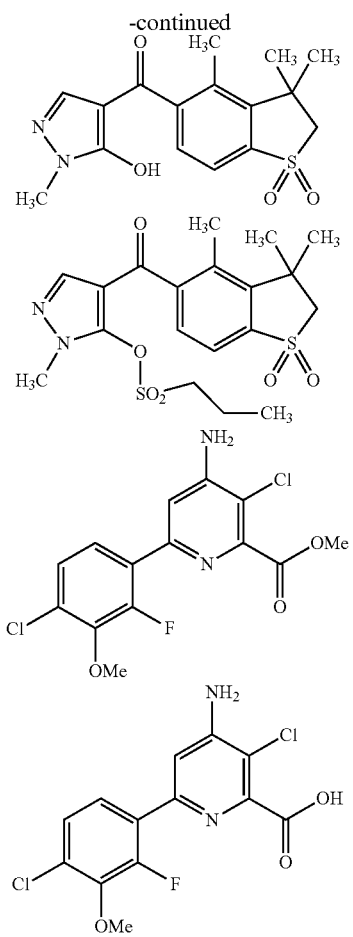

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It may vary within wide limits, for example between 0.001 and 1.0 kg/ha or more of active substance, but it is preferably between 0.005 and 750 g/ha.

The examples which follow illustrate the invention.

A. CHEMICAL EXAMPLES

Synthesis of 2-bromo-3-methoxy-N-(1-methyl-1H-tetrazol-5-yl)-4-nitrobenzamide (Example 1-1 In The Table)

1. Stage: Synthesis of ethyl 2-bromo-3-methoxy-4-nitrobenzoate

Ethyl 2-bromo-3-hydroxy-4-nitrobenzoate (630 mg, 2.17 mmol, preparation described in WO 90/05712 A1). Iodomethane (203 μl, 3.26 mmol) and CsCO₃ (1.06 g, 3.26 mmol) are dissolved in acetonitrile (18 ml) in a microwave container and heated for 45 minutes at 140° C., with microwave irradiation. The reaction mixture is filtered and taken up in water. The aqueous phase is extracted repeatedly with ethyl acetate. The combined organic phases are washed with NaOH solution (5 M in water) and with saturated NaCl solution, dried over MgSO$_4$ and concentrated. The crude product is dissolved in methanol (30 ml), THF (30 ml) and water (7.5 ml) and treated with 887 μl (4.44 mmol) of NaOH solution (5 M in water). The reaction mixture is stirred overnight at room temperature (RT). Thereafter, the solution is concentrated and the residue is treated with water. The aqueous phase is washed with diethyl ether. The aqueous phase is rendered acidic with HCl solution (2M in water) and extracted repeatedly with ethyl acetate. The combined organic phases are dried over magnesium sulfate and concentrated. This gives 503 mg (1.82 mmol, yield 84%) of 2-bromo-3-methoxy-4-nitrobenzoic acid.

$^1$H NMR, CDCl$_3$, 400 MHz: 7.79 (d, 1H), 7.72 (d, 1H), 4.06 (s, 3H).

2. Stage: Synthesis of 2-bromo-3-methoxy-N-(1-methyl-1H-tetrazol-5-yl)-4-nitrobenzamide 2-bromo-3-methoxy-4-nitrobenzoic acid (95 mg, 0.344 mmol) and 1-methyl-1H-tetrazol-5-amine (44 mg, 0.447 mmol) are dissolved in pyridine (6 ml). Oxalyl chloride (41 μl, 0.465 mmol) is slowly added dropwise, and the reaction mixture is subsequently warmed to 65° C. for 2 hours. The solvent is stripped off and the residue is separated by preparative HPLC. This gives 59 mg (0.165 mmol, yield 48%) of 2-bromo-3-methoxy-N-(1-methyl-1H-tetrazol-5-yl)-4-nitrobenzamide.

$^1$H NMR, DMSO-d6, 400 MHz: 11.99 (bs, 1H), 8.13 (d, 1H), 7.71 (d, 1H), 4.04 (s, 3H), 3.97 (s, 3H).

The examples listed in the tables below were prepared analogously to the abovementioned methods or are obtainable analogously to the abovementioned methods. The compounds listed in the tables below are very particularly preferred.

The abbreviations used mean:
Et=Ethyl Me=Methyl i-Pr=Isopropyl

TABLE 1

Compounds according to the invention of the general formula (I) in which Z is Z$^1$, B is N and R is a methyl group and W is hydrogen and A is CY.

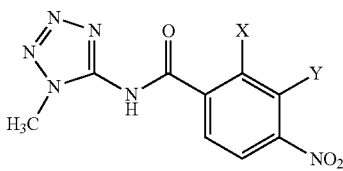

| No. | X | Y | Physical data |
|---|---|---|---|
| 1-1 | Br | OMe | 1H NMR, DMSO-d6, 400 MHz: 11.99 (bs, 1H), 8.13 (d, 1H), 7.71 (d, 1H), 4.04 (s, 3H), 3.97 (s, 3H) |
| 1-2 | Br | OEt | |
| 1-3 | Br | OPr | |
| 1-4 | Br | O-i-Pr | |
| 1-5 | Br | cyclopropylmethoxy | H NMR, CDCl3, 400 MHz: 7.79 (d, 1H), 7.50 (d, 1H), 4.16 (s, 3H), 4.06 (d, 2H), 1.36-1.39 (m, 1H), 0.64-0.69 (m, 2H), 0.38-0.42 (m, 2H) |
| 1-6 | Br | 2-fluorethoxy | |
| 1-7 | Br | 2,2-difluoroethoxy | |
| 1-8 | Br | 2,2,2-trifluoroethoxy | |
| 1-9 | Br | OCHF$_2$ | |
| 1-10 | Br | OCH$_2$F | |
| 1-11 | Br | OCF$_3$ | |
| 1-12 | Br | SO$_2$Me | |
| 1-13 | Br | SOMe | |
| 1-14 | Br | SMe | |
| 1-15 | Br | SO$_2$Et | |
| 1-16 | Br | SOEt | |
| 1-17 | Br | Set | |
| 1-18 | Br | O(CH$_2$)$_2$OMe | |
| 1-19 | Br | O(CH$_2$)$_3$OMe | 1H NMR, DMSO-d6, 400 MHz: 12.00 (bs, 1H), 8.12 (d, 1H), 7.73 (d, 1H), 4.17 (t, 2H), 4.04 (s, 3H), 3.50 (t, 2H), 3.26 (s, 3H), 2.00 (quin, 2H) |
| 1-20 | Br | O(CH$_2$)$_2$OEt | 1H NMR, CDCl3, 400 MHz: 10.15 (bs, 1H), 7.90 (d, 1H), 7.51 (d, 1H), 4.39 (t, 2H), 3.83 (t, 2H), 3.56 (q, 2H), 1.20 (t, 3H) |
| 1-21 | Br | O(CH$_2$)$_3$OEt | |
| 1-22 | Br | O(CH$_2$)$_2$SMe | |
| 1-23 | Br | O(CH$_2$)$_2$SOMe | |
| 1-24 | Br | O(CH$_2$)$_2$SO$_2$Me | |
| 1-25 | Br | O(CH$_2$)$_3$SMe | 1H NMR, DMSO-d6, 400 MHz: 12.00 (bs, 1H), 8.11 (d, 1H), 7.69 (d, 1H), 4.20 (t, 2H), 4.03 (s, 3H), 2.65 (t, 2H), 2.08 (s, 3H), 2.06 (quin, 2H) |
| 1-26 | Br | O(CH$_2$)$_3$SOMe | |
| 1-27 | Br | O(CH$_2$)$_3$SO$_2$Me | |
| 1-28 | Br | O(CH$_2$)$_2$SEt | |
| 1-29 | Br | O(CH$_2$)$_2$SOEt | |
| 1-30 | Br | O(CH$_2$)$_2$SO$_2$Et | |
| 1-31 | Br | O(CH$_2$)$_3$SEt | |
| 1-32 | Br | O(CH$_2$)$_3$SOEt | |
| 1-33 | Br | O(CH$_2$)$_3$SO$_2$Et | |
| 1-34 | Br | 1,4-dioxan-2-ylmethoxy | 1H NMR, DMSO-d6, 400 MHz: 11.88 (bs, 1H), 8.10 (d, 1H), 7.70 (d, 1H), 4.14 (d, 2H), 4.03 (s, 3H), 3.77-3.90 (m, 2H), 3.60-3.71 (m, 2H), 3.40-3.60 (m, 3H) |
| 1-35 | Br | 1,3-dioxolan-2-ylmethoxy | |
| 1-36 | Br | tetrahydrofuran-2-ylmethoxy | |
| 1-37 | Br | OCH$_2$(CO)NMe$_2$ | |
| 1-38 | Br | O(CH$_2$)$_2$NHSO$_2$Me | |
| 1-39 | Br | 4,5-dihydro-3-isoxazolyl | |
| 1-40 | Br | H | 1H NMR, CDCl$_3$, 400 MHz: 8.57 (d, 1H), 8.32 (dd, 1H), 7.87 (d, 1H), 4.16 (s, 3H) |
| 1-41 | Br | Me | |
| 1-42 | Br | (2,2,2-trifluoroethoxy)methyl | |
| 1-43 | Br | (RS)-tetrahydro-2-furyl-methoxymethyl | |
| 1-44 | Cl | OMe | 1H NMR, DMSO-d6, 400 MHz: 12.00 (bs, 1H), 8.10 (d, 1H), 7.76 (d, 1H), 4.02 (s, 3H), 3.99 (s, 3H) |
| 1-45 | Cl | OEt | |
| 1-46 | Cl | OPr | |
| 1-47 | Cl | O-i-Pr | |
| 1-48 | Cl | cyclopropylmethoxy | 1H NMR, CDCl3, 400 MHz: 0.37-0.40 (m, 2H), 0.63-0.70 (m, 2H), 1.32-1.39 (m, 1H), 4.08 (d, 2H), 4.12 (s, 3H), 7.61 (d, 1H), 7.82 (d, 1H), 9.46 (bs, 1H) |

TABLE 1-continued

Compounds according to the invention of the general formula (I) in which Z is $Z^1$, B is N and R is a methyl group and W is hydrogen and A is CY.

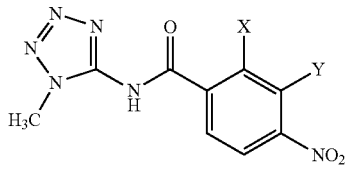

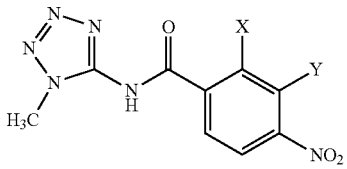

| No. | X | Y | Physical data |
|---|---|---|---|
| 1-49 | Cl | 2-fluoroethoxy | |
| 1-50 | Cl | 2,2-difluoroethoxy | |
| 1-51 | Cl | 2,2,2-trifluoroethoxy | |
| 1-52 | Cl | $OCHF_2$ | |
| 1-53 | Cl | $OCH_2F$ | |
| 1-54 | Cl | $OCF_3$ | |
| 1-55 | Cl | $SO_2Me$ | |
| 1-56 | Cl | SOMe | |
| 1-57 | Cl | SMe | |
| 1-58 | Cl | $SO_2Et$ | |
| 1-59 | Cl | SOEt | |
| 1-60 | Cl | Set | |
| 1-61 | Cl | $O(CH_2)_2OMe$ | 1H NMR, CDCl3, 400 MHz: 11.15 (bs, 1H), 7.90 (d, 1H), 7.51 (d, 1H), 4.37-4.40 (m ,2H), 4.16 (s, 3H), 3.78-3.80 (m, 2H), 3.41 (s, 3H) |
| 1-62 | Cl | $O(CH_2)_3OMe$ | 1H NMR, CDCl3, 400 MHz: 10.55 (bs, 1H), 7.81 (d, 1H), 7.58 (d, 1H), 4.32 (t, 2H), 4.14 (s, 3H), 3.60 (t, 2H), 3.37 (s, 3H), 2.13 (quin, 2H) |
| 1-63 | Cl | $O(CH_2)_2OEt$ | |
| 1-64 | Cl | $O(CH_2)_3OEt$ | |
| 1-65 | Cl | $O(CH_2)_2SMe$ | |
| 1-66 | Cl | $O(CH_2)_2SOMe$ | |
| 1-67 | Cl | $O(CH_2)_2SO_2Me$ | |
| 1-68 | Cl | $O(CH_2)_3SMe$ | 1H NMR, DMSO-d6, 400 MHz: 12.00 (bs, 1H), 8.09 (d, 1H), 7.73 (d, 1H), 4.23 (t, 2H), 4.02 (s, 3H), 2.64 (t, 2H), 2.07 (s, 3H), 2.03 (quin, 2H) |
| 1-69 | Cl | $O(CH_2)_3SOMe$ | |
| 1-70 | Cl | $O(CH_2)_3SO_2Me$ | |
| 1-71 | Cl | $O(CH_2)_2SEt$ | |
| 1-72 | Cl | $O(CH_2)_2SOEt$ | |
| 1-73 | Cl | $O(CH_2)_2SO_2Et$ | |
| 1-74 | Cl | $O(CH_2)_3SEt$ | |
| 1-75 | Cl | $O(CH_2)_3SOEt$ | |
| 1-76 | Cl | $O(CH_2)_3SO_2Et$ | |
| 1-77 | Cl | 1,4-dioxan-2-ylmethoxy | 1H NMR, DMSO-d6, 400 MHz: 11.99 (bs, 1H), 8.07 (d, 1H), 7.73 (d, 1H), 4.16 (d, 2H), 4.01 (s, 3H), 3.75-3.87 (m, 2H), 3.60-3.71 (m, 2H), 3.38-3.60 (m, 3H) |
| 1-78 | Cl | 1,3-dioxolan-2-ylmethoxy | 1H NMR, DMSO-d6, 400 MHz: 12.00 (bs, 1H), 8.08 (d, 1H), 7.74 (d, 1H), 5.18 (t, 1H), 4.16 (d, 2H), 4.01 (s, 3H), 3.87-3.93 (m, 2H), 3.80-3.87 (m, 2H) |
| 1-79 | Cl | tetrahydrofuran-2-yl-methoxy | 1H NMR, DMSO-d6, 400 MHz: 11.99 (bs, 1H), 8.07 (d, 1H), 7.73 (d, 1H), 4.10-4.14 (m, 3H), 4.02 (s, 3H), 3.71-3.75 (m, 1H), 3.65-3.68 (m, 1H), 1.93-2.01 (m, 1H), 1.78-1.90 (m, 2H), 1.65-1.73 (m, 1H) |
| 1-80 | Cl | $OCH_2(CO)NMe_2$ | |
| 1-81 | Cl | $O(CH_2)_2NHSO_2Me$ | |
| 1-82 | Cl | 4,5-dihydro-3-isoxazolyl | |
| 1-83 | Cl | Me | |
| 1-84 | Cl | (2,2,2-trifluoroethoxy)methyl | |
| 1-85 | Cl | (RS)-tetrahydro-2-furyl-methoxymethyl | |
| 1-86 | Me | OMe | H NMR, DMSO-d6, 400 MHz: 11.78 (bs, 1H), 7.78 (d, 1H), 7.60 (d, 1H), 4.00 (s, 3H), 3.86 (s, 3H), 2.40 (s, 3H) |
| 1-87 | Me | OEt | H NMR, DMSO-d6, 400 MHz: 11.64 (bs, 1H), 7.90 (d, 1H), 7.60 (d, 1H), 4.35 (q, 2H), 3.87 (s, 3H), 2.40 (s, 3H), 1.48 (t, 3H) |
| 1-88 | Me | OPr | |
| 1-89 | Me | O-i-Pr | |
| 1-90 | Me | cyclopropylmethoxy | |
| 1-91 | Me | 2-fluoroethoxy | |
| 1-92 | Me | 2,2-difluoroethoxy | |
| 1-93 | Me | 2,2,2-trifluoroethoxy | |
| 1-94 | Me | $OCHF_2$ | |
| 1-95 | Me | $OCH_2F$ | |
| 1-96 | Me | $OCF_3$ | |
| 1-97 | Me | $SO_2Me$ | |
| 1-98 | Me | SOMe | |
| 1-99 | Me | SMe | |
| 1-100 | Me | $SO_2Et$ | |
| 1-101 | Me | SOEt | |
| 1-102 | Me | Set | |
| 1-103 | Me | $O(CH_2)_2OMe$ | 1H NMR, CDCl3, 400 MHz: 10.40 (bs, 1H), 7.77 (d, 1H), 7.60 (d, 1H), 4.19-4.21 (m, 2H), 4.12 (s, 3H), 3.73-3.76 (m, 2H), 3.42 (s, 3H), 2.56 (s, 3H) |
| 1-104 | Me | $O(CH_2)_3OMe$ | 1H NMR, CDCl3, 400 MHz: 10.54 (bs, 1H), 7.75 (d, 1H), 7.61 (d, 1H), 4.12 (t, 2H), 4.12 (s, 3H), 3.59 (t, 2H), 3.37 (s, 3H), 3.53 (s, 3H), 2.09 (quin, 2H) |
| 1-105 | Me | $O(CH_2)_2OEt$ | |
| 1-106 | Me | $O(CH_2)_3OEt$ | |
| 1-107 | Me | $O(CH_2)_2SMe$ | |
| 1-108 | Me | $O(CH_2)_2SOMe$ | |
| 1-109 | Me | $O(CH_2)_2SO_2Me$ | |
| 1-110 | Me | $O(CH_2)_3SMe$ | |
| 1-111 | Me | $O(CH_2)_3SOMe$ | |
| 1-112 | Me | $O(CH_2)_3SO_2Me$ | |
| 1-113 | Me | $O(CH_2)_2SEt$ | |
| 1-114 | Me | $O(CH_2)_2SOEt$ | |
| 1-115 | Me | $O(CH_2)_2SO_2Et$ | |
| 1-116 | Me | $O(CH_2)_3SEt$ | |
| 1-117 | Me | $O(CH_2)_3SOEt$ | |
| 1-118 | Me | $O(CH_2)_3SO_2Et$ | |
| 1-119 | Me | 1,4-dioxan-2-ylmethoxy | H NMR, DMSO-d6, 400 MHz: 11.79 (bs, 1H), 7.88 (d, 1H), 7.59 (d, 1H), 4.00 (s, 3H), 3.98 (d, 2H), 3.80-3.82 (m, 1H), 3.75-3.80 (m, 1H), 3.71-3.73 (m, 1H), 3.64-3.66 (m, 1H), 3.57-3.62 (m, 1H), 3.45-3.50 (m, 1H), 3.38-3.40 (m, 1H), 2.40 (s, 3H) |
| 1-120 | Me | 1,3-dioxolan-2-ylmethoxy | |
| 1-121 | Me | tetrahydrofuran-2-yl-methoxy | H NMR, DMSO-d6, 400 MHz: 11.70 (bs, 1H), 7.88 (d, 1H), 7.59 (d, 1H), 4.10-4.16 (m, 1H), 4.00 (s, 3H), 3.89-3.97 (m, 2H), 3.72-3.80 (m, 1H), 3.64-3.72 |

TABLE 1-continued

Compounds according to the invention of the general formula (I) in which Z is $Z^1$, B is N and R is a methyl group and W is hydrogen and A is CY.

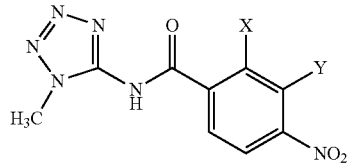

| No. | X | Y | Physical data |
|---|---|---|---|
| 1-122 | Me | OCH$_2$(CO)NMe$_2$ | (m, 1H), 3.31 (s, 3H), 2.41 (s, 3H), 1.93-1.98 (m, 1H), 1.81-1.87 (m, 2H), 1.62-1.67 (m, 1H) H NMR, DMSO-d6, 400 MHz: 7.71 (d, 1H), 7.64 (d, 1H), 4.70 (s, 2H), 3.89 (s, 3H), 2.87 (s, 3H), 2.83 (s, 3H), 2.39 (s, 3H) |
| 1-123 | Me | O(CH$_2$)$_2$NHSO$_2$Me | 1H NMR, DMSO-d6, 400 MHz: 11.77 (bs, 1H), 7.91 (d, 1H), 7.61 (d, 1H), 7.35 (t, 1H), 4.01-4.06 (m, 2H), 4.01 (s, 3H), 3.28-2.42 (m, 2H), 3.00 (s, 3H), 2.43 (s, 3H) |
| 1-124 | Me | 4,5-dihydro-3-isoxazolyl | |
| 1-125 | Me | H | |
| 1-126 | Me | Me | |
| 1-127 | Me | (2,2,2-trifluoro-ethoxy)methyl | |
| 1-128 | Me | (RS)-tetrahydro-2-furyl-methoxymethyl | |
| 1-129 | OMe | OMe | |
| 1-130 | OMe | OEt | |
| 1-131 | OMe | OPr | |
| 1-132 | OMe | O-i-Pr | |
| 1-133 | OMe | cyclopropylmethoxy | |
| 1-134 | OMe | 2-fluoroethoxy | |
| 1-135 | OMe | 2,2-difluoroethoxy | |
| 1-136 | OMe | 2,2,2-trifluoroethoxy | |
| 1-137 | OMe | OCHF$_2$ | |
| 1-138 | OMe | OCH$_2$F | |
| 1-139 | OMe | OCF$_3$ | |
| 1-140 | OMe | SO$_2$Me | |
| 1-141 | OMe | SOMe | |
| 1-142 | OMe | SMe | |
| 1-143 | OMe | SO$_2$Et | |
| 1-144 | OMe | SOEt | |
| 1-145 | OMe | SEt | |

TABLE 1-continued

Compounds according to the invention of the general formula (I) in which Z is $Z^1$, B is N and R is a methyl group and W is hydrogen and A is CY.

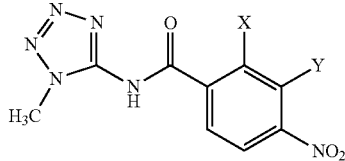

| No. | X | Y | Physical data |
|---|---|---|---|
| 1-146 | OMe | O(CH$_2$)$_2$OMe | |
| 1-147 | OMe | O(CH$_2$)$_3$OMe | |
| 1-148 | OMe | O(CH$_2$)$_2$OEt | |
| 1-149 | OMe | O(CH$_2$)$_3$OEt | |
| 1-150 | OMe | O(CH$_2$)$_2$SMe | |
| 1-151 | OMe | O(CH$_2$)$_2$SOMe | |
| 1-152 | OMe | O(CH$_2$)$_2$SO$_2$Me | |
| 1-153 | OMe | O(CH$_2$)$_3$SMe | |
| 1-154 | OMe | O(CH$_2$)$_3$SOMe | |
| 1-155 | OMe | O(CH$_2$)$_3$SO$_2$Me | |
| 1-156 | OMe | O(CH$_2$)$_2$SEt | |
| 1-157 | OMe | O(CH$_2$)$_2$SOEt | |
| 1-158 | OMe | O(CH$_2$)$_2$SO$_2$Et | |
| 1-159 | OMe | O(CH$_2$)$_3$SEt | |
| 1-160 | OMe | O(CH$_2$)$_3$SOEt | |
| 1-161 | OMe | O(CH$_2$)$_3$SO$_2$Et | |
| 1-162 | OMe | 1,4-dioxan-2-ylmethoxy | |
| 1-163 | OMe | 1,3-dioxolan-2-ylmethoxy | |
| 1-164 | OMe | tetrahydrofuran-2-yl-methoxy | |
| 1-165 | OMe | OCH$_2$(CO)NMe$_2$ | H NMR, DMSO-d6, 400 MHz: 11.90 (bs, 1H), 7.78 (d, 1H), 7.44 (d, 1H), 4.87 (s, 2H), 4.00 (s, 3H), 3.89 (s, 3H), 2.91 (s, 3H), 2.81 (s, 3H) |
| 1-166 | OMe | O(CH$_2$)$_2$NHSO$_2$Me | |
| 1-167 | OMe | 4,5-dihydro-3-isoxazolyl | |
| 1-168 | OMe | H | |
| 1-169 | OMe | Me | |
| 1-170 | OMe | (2,2,2-trifluoroethoxy)methyl | |
| 1-171 | OMe | (RS)-tetrahydro-2-furyl-methoxymethyl | |
| 1-172 | NO$_2$ | H | 1H NMR, DMSO-d6, 400 MHz: 12.22 (bs, 1H), 8.89 (d, 1H), 8.73 (d, 1H), 8.22 (bs, 1H), 4.03 (s, 3H) |
| 1-173 | CF$_3$ | H | 1H NMR, CDCl$_3$, 400 MHz: 8.68 (d, 1H), 8.56 (dd, 1H), 7.98 (d, 1H), 4.16 (s, 3H) |

TABLE 2

Compounds according to the invention of the general formula (I) in which Z is $Z^1$, B is N and R is an ethyl group and W is hydrogen and A is CY.

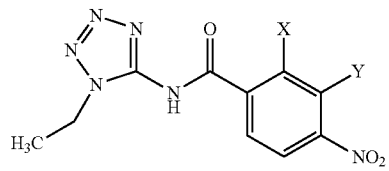

| No. | X | Y | Physical data |
|---|---|---|---|
| 2-1 | Br | OMe | 1H NMR, DMSO-d6, 400 MHz: 11.86 (bs, 1H), 8.13 (d, 1H), 7.72 (d, 1H), 4.40 (q, 2H), 3.97 (s, 3H), 1.48 (t, 3H) |
| 2-2 | Br | OEt | |
| 2-3 | Br | OPr | |
| 2-4 | Br | O-i-Pr | |
| 2-5 | Br | cyclopropylmethoxy | |
| 2-6 | Br | 2-fluoroethoxy | |

TABLE 2-continued

Compounds according to the invention of the general formula (I) in which
Z is $Z^1$, B is N and R is an ethyl group and W is hydrogen and A is CY.

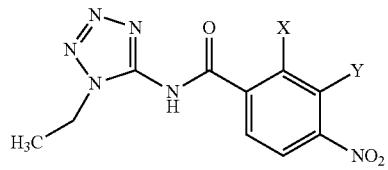

| No. | X | Y | Physical data |
|---|---|---|---|
| 2-7 | Br | 2,2-difluoroethoxy | |
| 2-8 | Br | 2,2,2-trifluoroethoxy | |
| 2-9 | Br | $OCHF_2$ | |
| 2-10 | Br | $OCH_2F$ | |
| 2-11 | Br | $OCF_3$ | |
| 2-12 | Br | $SO_2Me$ | |
| 2-13 | Br | SOMe | |
| 2-14 | Br | SMe | |
| 2-15 | Br | $SO_2Et$ | |
| 2-16 | Br | SOEt | |
| 2-17 | Br | SEt | |
| 2-18 | Br | $O(CH_2)_2OMe$ | |
| 2-19 | Br | $O(CH_2)_3OMe$ | 1H NMR, CDCl3, 400 MHz: 10.10 (bs, 1H), 7.87 (d, 1H), 7.50 (d, 1H), 4.51 (q, 2H), 4.29 (t, 2H), 3.60 (t, 2H), 3.38 (s, 3H), 2.14 (quin, 2H), 1.63 (t, 3H) |
| 2-20 | Br | $O(CH_2)_2OEt$ | 1H NMR, CDCl3, 400 MHz: 10.80 (bs, 1H), 7.89 (d, 1H), 7.49 (d, 1H), 4.52 (q, 2H), 4.39 (t, 2H), 3.82 (t, 2H), 3.56 (q, 2H), 1.64 (t, 3H), 1.20 (t, 3H) |
| 2-21 | Br | $O(CH_2)_3OEt$ | |
| 2-22 | Br | $O(CH_2)_2SMe$ | |
| 2-23 | Br | $O(CH_2)_2SOMe$ | |
| 2-24 | Br | $O(CH_2)_2SO_2Me$ | |
| 2-25 | Br | $O(CH_2)_3SMe$ | 1H NMR, DMSO-d6, 400 MHz: 11.86 (bs, 1H), 8.12 (d, 1H), 7.70 (d, 1H), 4.39 (q, 2H), 4.20 (t, 2H), 2.65 (t, 2H), 2.08 (s, 3H), 2.06 (quin, 2H), 1.49 (t, 3H) |
| 2-26 | Br | $O(CH_2)_3SOMe$ | |
| 2-27 | Br | $O(CH_2)_3SO_2Me$ | |
| 2-28 | Br | $O(CH_2)_2SEt$ | |
| 2-29 | Br | $O(CH_2)_2SOEt$ | |
| 2-30 | Br | $O(CH_2)_2SO_2Et$ | |
| 2-31 | Br | $O(CH_2)_3SEt$ | |
| 2-32 | Br | $O(CH_2)_3SOEt$ | |
| 2-33 | Br | $O(CH_2)_3SO_2Et$ | |
| 2-34 | Br | 1,4-dioxan-2-ylmethoxy | 1H NMR, DMSO-d6, 400 MHz: 11.86 (bs, 1H), 8.10 (d, 1H), 7.69 (d, 1H), 4.39 (q, 2H), 4.09-4.15 (m, 2H), 3.78-3.90 (m, 2H), 3.62-3.72 (m, 2H), 3.40-3.62 (m, 3H), 1.48 (t, 3H) |
| 2-35 | Br | 1,3-dioxolan-2-ylmethoxy | |
| 2-36 | Br | tetrahydrofuran-2-yl-methoxy | |
| 2-37 | Br | $OCH_2(CO)NMe_2$ | |
| 2-38 | Br | $O(CH_2)_2NHSO_2Me$ | |
| 2-39 | Br | 4,5-dihydro-3-isoxazolyl | |
| 2-40 | Br | H | 1H NMR, DMSO-d6, 400 MHz: 1.95 (bs, 1H), 8.57 (d, 1H), 8.37 (dd, 1H), 8.01 (d, 1H), 4.40 (q, 2H), 1.49 (t, 3H) |
| 2-41 | Br | Me | |
| 2-42 | Br | (2,2,2-trifluoroethoxy)methyl | |
| 2-43 | Br | (RS)-tetrahydro-2-furylmethoxymethyl | |
| 2-44 | Cl | OMe | 1H NMR, DMSO-d6, 400 MHz: 1.89 (bs, 1H), 8.10 (d, 1H), 7.75 (d, 1H), 4.38 (q, 2H), 3.99 (s, 3H), 1.48 (t, 3H) |
| 2-45 | Cl | OEt | |
| 2-46 | Cl | OPr | |
| 2-47 | Cl | O-i-Pr | |
| 2-48 | Cl | cyclopropylmethoxy | |
| 2-49 | Cl | 2-fluoroethoxy | |
| 2-50 | Cl | 2,2-difluoroethoxy | |
| 2-51 | Cl | 2,2,2-trifluoroethoxy | |
| 2-52 | Cl | $OCHF_2$ | |
| 2-53 | Cl | $OCH_2F$ | |
| 2-54 | Cl | $OCF_3$ | |
| 2-55 | Cl | $SO_2Me$ | |

TABLE 2-continued

Compounds according to the invention of the general formula (I) in which Z is $Z^1$, B is N and R is an ethyl group and W is hydrogen and A is CY.

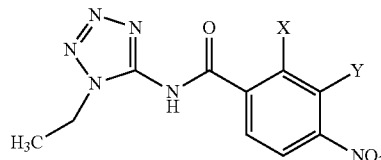

| No. | X | Y | Physical data |
|---|---|---|---|
| 2-56 | Cl | SOMe | |
| 2-57 | Cl | SMe | |
| 2-58 | Cl | $SO_2Et$ | |
| 2-59 | Cl | SOEt | |
| 2-60 | Cl | Set | |
| 2-61 | Cl | $O(CH_2)_2OMe$ | 1H NMR, CDCl3, 400 MHz: 10.50 (bs, 1H), 7.89 (d, 1H), 7.51 (d, 1H), 4.52 (q, 2H), 4.38-4.40 (m, 2H), 3.78-3.80 (m, 2H), 3.41 (s, 3H), 1.65 (t, 3H) |
| 2-62 | Cl | $O(CH_2)_3OMe$ | 1H NMR, CDCl3, 400 MHz: 10.40 (bs, 1H), 7.82 (d, 1H), 7.58 (d, 1H), 4.49 (q, 2H), 4.32 (t, 2H), 3.60 (t, 2H), 3.37 (s, 3H), 2.13 (quin, 2H), 1.64 (t, 3H) |
| 2-63 | Cl | $O(CH_2)_2OEt$ | |
| 2-64 | Cl | $O(CH_2)_3OEt$ | |
| 2-65 | Cl | $O(CH_2)_2SMe$ | |
| 2-66 | Cl | $O(CH_2)_2SOMe$ | |
| 2-67 | Cl | $O(CH_2)_2SO_2Me$ | |
| 2-68 | Cl | $O(CH_2)_3SMe$ | 1H NMR, DMSO-d6, 400 MHz: 11.90 (bs, 1H), 8.09 (d, 1H), 7.72 (d, 1H), 4.37 (q, 2H), 4.23 (t, 2H), 2.64 (t, 2H), 2.08 (s, 3H), 2.03 (quin, 2H), 1.48 (t, 3H) |
| 2-69 | Cl | $O(CH_2)_3SOMe$ | |
| 2-70 | Cl | $O(CH_2)_3SO_2Me$ | |
| 2-71 | Cl | $O(CH_2)_2SEt$ | |
| 2-72 | Cl | $O(CH_2)_2SOEt$ | |
| 2-73 | Cl | $O(CH_2)_2SO_2Et$ | |
| 2-74 | Cl | $O(CH_2)_3SEt$ | |
| 2-75 | Cl | $O(CH_2)_3SOEt$ | |
| 2-76 | Cl | $O(CH_2)_3SO_2Et$ | |
| 2-77 | Cl | 1,4-dioxan-2-ylmethoxy | 1H NMR, DMSO-d6, 400 MHz: 11.88 (bs, 1H), 8.07 (d, 1H), 7.73 (d, 1H), 4.37 (q, 2H), 4.16 (d, 2H), 3.75-3.86 (m, 2H), 3.60-3.71 (m, 2H), 3.39-3.60 (m, 3H) |
| 2-78 | Cl | 1,3-dioxolan-2-ylmethoxy | |
| 2-79 | Cl | tetrahydrofuran-2-yl-methoxy | |
| 2-80 | Cl | $OCH_2(CO)NMe_2$ | |
| 2-81 | Cl | $O(CH_2)_2NHSO_2Me$ | |
| 2-82 | Cl | 4,5-dihydro-3-isoxazolyl | |
| 2-83 | Cl | H | |
| 2-84 | Cl | Me | |
| 2-85 | Cl | (2,2,2-trifluoroethoxy)methyl | |
| 2-86 | Cl | (RS)-tetrahydro-2-furylmethoxymethyl | |
| 2-87 | Me | OMe | |
| 2-88 | Me | OEt | H NMR, DMSO-d6, 400 MHz: 11.86 (bs, 1H), 7.73 (d, 1H), 7.67 (d, 1H), 4.26 (q, 2H), 4.03 (q, 2H), 2.41 (s, 3H), 1.43 (t, 3H), 1.28 (t, 3H) |
| 2-89 | Me | OPr | |
| 2-90 | Me | O-i-Pr | |
| 2-91 | Me | cyclopropylmethoxy | |
| 2-92 | Me | 2-fluoroethoxy | |
| 2-93 | Me | 2,2-difluoroethoxy | |
| 2-94 | Me | 2,2,2-trifluoroethoxy | |
| 2-95 | Me | $OCHF_2$ | |
| 2-96 | Me | $OCH_2F$ | |
| 2-97 | Me | $OCF_3$ | |
| 2-98 | Me | $SO_2Me$ | |
| 2-99 | Me | SOMe | |
| 2-100 | Me | SMe | |
| 2-101 | Me | $SO_2Et$ | |
| 2-102 | Me | SOEt | |
| 2-103 | Me | Set | |
| 2-104 | Me | $O(CH_2)_2OMe$ | 1H NMR, CDCl3, 400 MHz: 10.30 (bs, 1H), 7.67 (d, 1H), 7.58 (d, 1H), 4.47 (q, 2H), 4.19-4.21 (m, 2H), 3.73-3.76 (m, |

TABLE 2-continued

Compounds according to the invention of the general formula (I) in which
Z is $Z^1$, B is N and R is an ethyl group and W is hydrogen and A is CY.

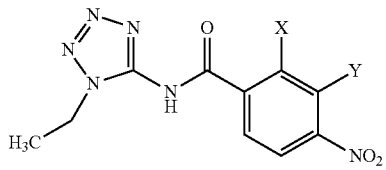

| No. | X | Y | Physical data |
|---|---|---|---|
|  |  |  | 2H), 3.42 (s, 3H), 2.56 (s, 3H), 1.64 (t, 3H) |
| 2-105 | Me | O(CH$_2$)$_3$OMe | 1H NMR, CDCl3, 400 MHz: 10.65 (bs, 1H), 7.75 (d, 1H), 7.61 (d, 1H), 4.47 (q, 2H), 4.12 (t, 2H), 3.59 (t, 2H), 3.37 (s, 3H), 2.53 (s, 3H), 2.09 (quin, 2H), 1.63 (t, 3H) |
| 2-106 | Me | O(CH$_2$)$_2$OEt |  |
| 2-107 | Me | O(CH$_2$)$_3$OEt |  |
| 2-108 | Me | O(CH$_2$)$_2$SMe | H-NMR, DMSO-d6, 400 MHz: 11.85 (bs, 1H), 7.75 (d, 1H), 7.68 (d, 1H), 4.26 (q, 2H), 4.12 (t, 2H), 2.82 (t, 2H), 2.41 (s, 3H), 2.13 (s, 3H), 1.43 (t, 3H) |
| 2-109 | Me | O(CH$_2$)$_2$SOMe |  |
| 2-110 | Me | O(CH$_2$)$_2$SO$_2$Me |  |
| 2-111 | Me | O(CH$_2$)$_3$SMe |  |
| 2-112 | Me | O(CH$_2$)$_3$SOMe |  |
| 2-113 | Me | O(CH$_2$)$_3$SO$_2$Me |  |
| 2-114 | Me | O(CH$_2$)$_2$SEt |  |
| 2-115 | Me | O(CH$_2$)$_2$SOEt |  |
| 2-116 | Me | O(CH$_2$)$_2$SO$_2$Et |  |
| 2-117 | Me | O(CH$_2$)$_3$SEt |  |
| 2-118 | Me | O(CH$_2$)$_3$SOEt |  |
| 2-119 | Me | O(CH$_2$)$_3$SO$_2$Et |  |
| 2-120 | Me | 1,4-dioxan-2-ylmethoxy | H NMR, DMSO-d6, 400 MHz: 11.88 (bs, 1H), 7.73 (d, 1H), 7.67 (d, 1H), 4.26 (q, 2H), 3.90-4.00 (m, 2H), 3.70-3.82 (m, 3H), 3.56-3.68 (m, 2H), 3.45-3.50 (m, 1H), 3.30-3.40 (m, 1H), 2.42 (s, 3H), 1.43 (t, 3H) |
| 2-121 | Me | 1,3-dioxolan-2-ylmethoxy | H NMR, DMSO-d6, 400 MHz: 11.87 (bs, 1H), 7.74 (d, 1H), 7.67 (d, 1H), 4.12 (t, 1H), 4.24 (q, 2H), 3.95-4.00 (m, 2H), 3.90-3.95 (m, 2H), 3.80-3.85 (m, 2H), 2.39 (s, 3H), 1.41 (t, 3H) |
| 2-122 | Me | tetrahydrofuran-2-yl-methoxy | H NMR, DMSO-d6, 400 MHz: 11.86 (bs, 1H), 7.73 (d, 1H), 7.67 (d, 1H), 4.26 (q, 2H), 4.05-4.13 (m, 1H), 3.93 (d, 2H), 3.74-3.93 (m, 1H), 3.65-3.71 (m, 1H), 2.07 (s, 3H), 1.90-2.00 (m, 1H), 1.78-1.90 (m, 2H), 1.59-1.66 (m, 1H), 1.43 (t, 3H) |
| 2-123 | Me | OCH$_2$(CO)NMe$_2$ | H NMR, DMSO-d6, 400 MHz: 1.89 (bs, 1H), 7.73 (d, 1H), 7.68 (d, 1H), 4.72 (s, 2H), 4.26 (q, 2H), 2.91 (s, 3H), 2.85 (s, 3H), 2.41 (s, 3H), 1.43 (t, 3H) |
| 2-124 | Me | O(CH$_2$)$_2$NHSO$_2$Me | 1H NMR, CDCl3, 400 MHz: 7.78 (d, 1H), 7.61 (d, 1H), 4.95 (bt, 1H), 4.48 (q, 2H), 4.22 (t, 2H), 3.60 (q, 2H), 3.04 (s, 3H), 2.55 (s, 3H), 1.64 (t, 3H) |
| 2-125 | Me | 4,5-dihydro-3-isoxazolyl |  |
| 2-126 | Me | H |  |
| 2-127 | Me | Me |  |
| 2-128 | Me | (2,2,2-trifluoroethoxy)methyl |  |
| 2-129 | Me | (RS)-tetrahydro-2-furylmethoxymethyl |  |
| 2-130 | OMe | OMe |  |
| 2-131 | OMe | OEt |  |
| 2-132 | OMe | OPr |  |
| 2-133 | OMe | O-i-Pr |  |
| 2-134 | OMe | cyclopropylmethoxy |  |
| 2-135 | OMe | 2-fluoroethoxy |  |
| 2-136 | OMe | 2,2-difluoroethoxy |  |
| 2-137 | OMe | 2,2,2-trifluoroethoxy |  |
| 2-138 | OMe | OCHF$_2$ |  |
| 2-139 | OMe | OCH$_2$F |  |
| 2-140 | OMe | OCF$_3$ |  |

TABLE 2-continued

Compounds according to the invention of the general formula (I) in which Z is $Z^1$, B is N and R is an ethyl group and W is hydrogen and A is CY.

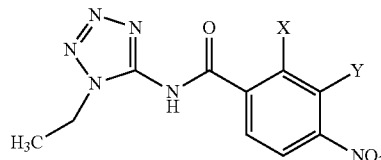

| No. | X | Y | Physical data |
|---|---|---|---|
| 2-141 | OMe | SO$_2$Me | |
| 2-142 | OMe | SOMe | |
| 2-143 | OMe | SMe | |
| 2-144 | OMe | SO$_2$Et | |
| 2-145 | OMe | SOEt | |
| 2-146 | OMe | SEt | |
| 2-147 | OMe | O(CH$_2$)$_2$OMe | |
| 2-148 | OMe | O(CH$_2$)$_3$OMe | |
| 2-149 | OMe | O(CH$_2$)$_2$OEt | |
| 2-150 | OMe | O(CH$_2$)$_3$OEt | |
| 2-151 | OMe | O(CH$_2$)$_2$SMe | |
| 2-152 | OMe | O(CH$_2$)$_2$SOMe | |
| 2-153 | OMe | O(CH$_2$)$_2$SO$_2$Me | |
| 2-154 | OMe | O(CH$_2$)$_3$SMe | |
| 2-155 | OMe | O(CH$_2$)$_3$SOMe | |
| 2-156 | OMe | O(CH$_2$)$_3$SO$_2$Me | |
| 2-157 | OMe | O(CH$_2$)$_2$SEt | |
| 2-158 | OMe | O(CH$_2$)$_2$SOEt | |
| 2-159 | OMe | O(CH$_2$)$_2$SO$_2$Et | |
| 2-160 | OMe | O(CH$_2$)$_3$SEt | |
| 2-161 | OMe | O(CH$_2$)$_3$SOEt | |
| 2-162 | OMe | O(CH$_2$)$_3$SO$_2$Et | |
| 2-163 | OMe | 1,4-dioxan-2-ylmethoxy | |
| 2-164 | OMe | 1,3-dioxolan-2-ylmethoxy | |
| 2-165 | OMe | tetrahydrofuran-2-yl-methoxy | |
| 2-166 | OMe | OCH$_2$(CO)NMe$_2$ | |
| 2-167 | OMe | O(CH$_2$)$_2$NHSO$_2$Me | |
| 2-168 | OMe | 4,5-dihydro-3-isoxazolyl | |
| 2-169 | OMe | H | |
| 2-170 | OMe | Me | |
| 2-171 | OMe | (2,2,2-trifluorethoxy)methyl | |
| 2-172 | OMe | (RS)-tetrahydro-2-furylmethoxymethyl | |
| 2-173 | CF$_3$ | H | 1H NMR, DMSO-d6, 400 MHz: 12.09 (bs, 1H), 8.68 (d, 1H), 8.61 (d, 1H), 8.24 (bd, 1H), 4.37 (q, 2H), 1.48 (t, 3H) |
| 2-174 | NO$_2$ | H | 1H NMR, DMSO-d6, 400 MHz: 12.12 (bs, 1H), 8.89 (d, 1H), 8.73 (d, 1H), 8.21 (bs, 1H), 4.39 (q, 2H), 1.49 (t, 3H) |

TABLE 3

Compounds according to the invention of the general formula (I) in which Z is $Z^1$, B is N and R is a propyl group and W is hydrogen and A is CY.

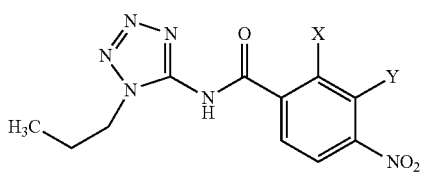

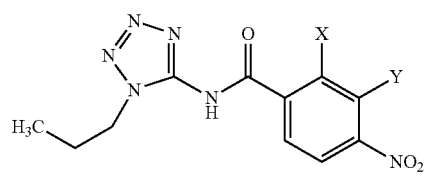

| No. | X | Y | Physical data |
|---|---|---|---|
| 3-1 | Br | OMe | |
| 3-2 | Br | OEt | |
| 3-3 | Br | OPr | |
| 3-4 | Br | O-i-Pr | |
| 3-5 | Br | cyclopropylmethoxy | |
| 3-6 | Br | 2-fluoroethoxy | |
| 3-7 | Br | 2,2-difluoroethoxy | |
| 3-8 | Br | 2,2,2-trifluoroethoxy | |
| 3-9 | Br | OCHF$_2$ | |
| 3-10 | Br | OCH$_2$F | |
| 3-11 | Br | OCF$_3$ | |
| 3-12 | Br | SO$_2$Me | |
| 3-13 | Br | SOMe | |
| 3-14 | Br | SMe | |
| 3-15 | Br | SO$_2$Et | |
| 3-16 | Br | SOEt | |
| 3-17 | Br | SEt | |
| 3-18 | Br | O(CH$_2$)$_2$OMe | |

TABLE 3-continued

Compounds according to the invention of the general formula (I) in which Z is $Z^1$, B is N and R is a propyl group and W is hydrogen and A is CY.

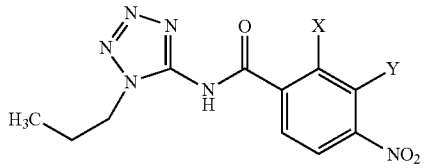

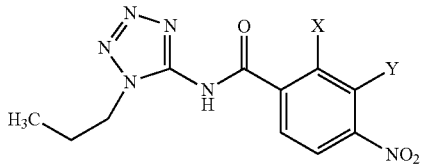

| No. | X | Y | Physical data |
|---|---|---|---|
| 3-19 | Br | O(CH$_2$)$_3$OMe | |
| 3-20 | Br | O(CH$_2$)$_2$OEt | |
| 3-21 | Br | O(CH$_2$)$_3$OEt | |
| 3-22 | Br | O(CH$_2$)$_2$SMe | |
| 3-23 | Br | O(CH$_2$)$_2$SOMe | |
| 3-24 | Br | O(CH$_2$)$_2$SO$_2$Me | |
| 3-25 | Br | O(CH$_2$)$_3$SMe | |
| 3-26 | Br | O(CH$_2$)$_3$SOMe | |
| 3-27 | Br | O(CH$_2$)$_3$SO$_2$Me | |
| 3-28 | Br | O(CH$_2$)$_2$SEt | |
| 3-29 | Br | O(CH$_2$)$_2$SOEt | |
| 3-30 | Br | O(CH$_2$)$_2$SO$_2$Et | |
| 3-31 | Br | O(CH$_2$)$_3$SEt | |
| 3-32 | Br | O(CH$_2$)$_3$SOEt | |
| 3-33 | Br | O(CH$_2$)$_3$SO$_2$Et | |
| 3-34 | Br | 1,4-dioxan-2-ylmethoxy | |
| 3-35 | Br | 1,3-dioxolan-2-ylmethoxy | |
| 3-36 | Br | tetrahydrofuran-2-yl-methoxy | |
| 3-37 | Br | OCH$_2$(CO)NMe$_2$ | |
| 3-38 | Br | O(CH$_2$)$_2$NHSO$_2$Me | |
| 3-39 | Br | 4,5-dihydro-3-isoxazolyl | |
| 3-40 | Br | H | |
| 3-41 | Br | Me | |
| 3-42 | Br | (2,2,2-trifluoroethoxy)methyl | |
| 3-43 | Br | (RS)-tetrahydro-2-furylmethoxymethyl | |
| 3-44 | Cl | OMe | |
| 3-45 | Cl | OEt | |
| 3-46 | Cl | OPr | |
| 3-47 | Cl | O-i-Pr | |
| 3-48 | Cl | cyclopropylmethoxy | |
| 3-49 | Cl | 2-fluoroethoxy | |
| 3-50 | Cl | 2,2-difluoroethoxy | |
| 3-51 | Cl | 2,2,2-trifluoroethoxy | |
| 3-52 | Cl | OCHF$_2$ | |
| 3-53 | Cl | OCH$_2$F | |
| 3-54 | Cl | OCF$_3$ | |
| 3-55 | Cl | SO$_2$Me | |
| 3-56 | Cl | SOMe | |
| 3-57 | Cl | SMe | |
| 3-58 | Cl | SO$_2$Et | |
| 3-59 | Cl | SOEt | |
| 3-60 | Cl | SEt | |
| 3-61 | Cl | O(CH$_2$)$_2$OMe | |
| 3-62 | Cl | O(CH$_2$)$_3$OMe | |
| 3-63 | Cl | O(CH$_2$)$_2$OEt | |
| 3-64 | Cl | O(CH$_2$)$_3$OEt | |
| 3-65 | Cl | O(CH$_2$)$_2$SMe | |
| 3-66 | Cl | O(CH$_2$)$_2$SOMe | |
| 3-67 | Cl | O(CH$_2$)$_2$SO$_2$Me | |
| 3-68 | Cl | O(CH$_2$)$_3$SMe | |
| 3-69 | Cl | O(CH$_2$)$_3$SOMe | |
| 3-70 | Cl | O(CH$_2$)$_3$SO$_2$Me | |
| 3-71 | Cl | O(CH$_2$)$_2$SEt | |
| 3-72 | Cl | O(CH$_2$)$_2$SOEt | |
| 3-73 | Cl | O(CH$_2$)$_2$SO$_2$Et | |
| 3-74 | Cl | O(CH$_2$)$_3$SEt | |
| 3-75 | Cl | O(CH$_2$)$_3$SOEt | |
| 3-76 | Cl | O(CH$_2$)$_3$SO$_2$Et | |
| 3-77 | Cl | 1,4-dioxan-2-ylmethoxy | |
| 3-78 | Cl | 1,3-dioxolan-2-ylmethoxy | |
| 3-79 | Cl | tetrahydrofuran-2-yl-methoxy | |
| 3-80 | Cl | OCH$_2$(CO)NMe$_2$ | |
| 3-81 | Cl | O(CH$_2$)$_2$NHSO$_2$Me | |
| 3-82 | Cl | 4,5-dihydro-3-isoxazolyl | |
| 3-83 | Cl | Me | |
| 3-84 | Cl | (2,2,2-trifluoromethoxy)methyl | |
| 3-85 | Cl | (RS)-tetrahydro-2-furylmethoxymethyl | |
| 3-86 | Me | OMe | |
| 3-87 | Me | OEt | |
| 3-88 | Me | OPr | |
| 3-89 | Me | O-i-Pr | |
| 3-90 | Me | cyclopropylmethoxy | |
| 3-91 | Me | 2-fluoroethoxy | |
| 3-92 | Me | 2,2-difluoroethoxy | |
| 3-93 | Me | 2,2,2-trifluoroethoxy | |
| 3-94 | Me | OCHF$_2$ | |
| 3-95 | Me | OCH$_2$F | |
| 3-96 | Me | OCF$_3$ | |
| 3-97 | Me | SO$_2$Me | |
| 3-98 | Me | SOMe | |
| 3-99 | Me | SMe | |
| 3-100 | Me | SO$_2$Et | |
| 3-101 | Me | SOEt | |
| 3-102 | Me | SEt | |
| 3-103 | Me | O(CH$_2$)$_2$OMe | |
| 3-104 | Me | O(CH$_2$)$_3$OMe | |
| 3-105 | Me | O(CH$_2$)$_2$OEt | |
| 3-106 | Me | O(CH$_2$)$_3$OEt | |
| 3-107 | Me | O(CH$_2$)$_2$SMe | |
| 3-108 | Me | O(CH$_2$)$_2$SOMe | |
| 3-109 | Me | O(CH$_2$)$_2$SO$_2$Me | |
| 3-110 | Me | O(CH$_2$)$_3$SMe | |
| 3-111 | Me | O(CH$_2$)$_3$SOMe | |
| 3-112 | Me | O(CH$_2$)$_3$SO$_2$Me | |
| 3-113 | Me | O(CH$_2$)$_2$SEt | |
| 3-114 | Me | O(CH$_2$)$_2$SOEt | |
| 3-115 | Me | O(CH$_2$)$_2$SO$_2$Et | |
| 3-116 | Me | O(CH$_2$)$_3$SEt | |
| 3-117 | Me | O(CH$_2$)$_3$SOEt | |
| 3-118 | Me | O(CH$_2$)$_3$SO$_2$Et | |
| 3-119 | Me | 1,4-dioxan-2-ylmethoxy | |
| 3-120 | Me | 1,3-dioxolan-2-ylmethoxy | |
| 3-121 | Me | tetrahydrofuran-2-yl-methoxy | |
| 3-122 | Me | OCH$_2$(CO)NMe$_2$ | |
| 3-123 | Me | O(CH$_2$)$_2$NHSO$_2$Me | |
| 3-124 | Me | 4,5-dihydro-3-isoxazolyl | |
| 3-125 | Me | H | |
| 3-126 | Me | Me | |
| 3-127 | Me | (2,2,2-trifluoroethoxy)methyl | |
| 3-128 | Me | (RS)-tetrahydro-2-furylmethoxymethyl | |
| 3-129 | OMe | OMe | |
| 3-130 | OMe | OEt | |
| 3-131 | OMe | OPr | |
| 3-132 | OMe | O-i-Pr | |
| 3-133 | OMe | cyclopropylmethoxy | |
| 3-134 | OMe | 2-fluoroethoxy | |
| 3-135 | OMe | 2,2-difluoroethoxy | |
| 3-136 | OMe | 2,2,2-trifluoroethoxy | |
| 3-137 | OMe | OCHF$_2$ | |
| 3-138 | OMe | OCH$_2$F | |
| 3-139 | OMe | OCF$_3$ | |
| 3-140 | OMe | SO$_2$Me | |
| 3-141 | OMe | SOMe | |
| 3-142 | OMe | SMe | |
| 3-143 | OMe | SO$_2$Et | |
| 3-144 | OMe | SOEt | |
| 3-145 | OMe | SEt | |
| 3-146 | OMe | O(CH$_2$)$_2$OMe | |
| 3-147 | OMe | O(CH$_2$)$_3$OMe | |
| 3-148 | OMe | O(CH$_2$)$_2$OEt | |
| 3-149 | OMe | O(CH$_2$)$_3$OEt | |
| 3-150 | OMe | O(CH$_2$)$_2$SMe | |

TABLE 3-continued

Compounds according to the invention of the general formula (I) in which Z is $Z^1$, B is N and R is a propyl group and W is hydrogen and A is CY.

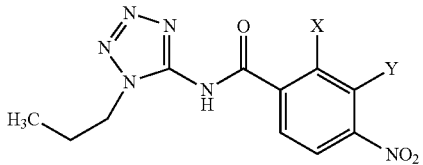

| No. | X | Y | Physical data |
|---|---|---|---|
| 3-151 | OMe | O(CH$_2$)$_2$SOMe | |
| 3-152 | OMe | O(CH$_2$)$_2$SO$_2$Me | |
| 3-153 | OMe | O(CH$_2$)$_3$SMe | |
| 3-154 | OMe | O(CH$_2$)$_3$SOMe | |
| 3-155 | OMe | O(CH$_2$)$_3$SO$_2$Me | |
| 3-156 | OMe | O(CH$_2$)$_2$SEt | |
| 3-157 | OMe | O(CH$_2$)$_2$SOEt | |
| 3-158 | OMe | O(CH$_2$)$_2$SO$_2$Et | |
| 3-159 | OMe | O(CH$_2$)$_3$SEt | |
| 3-160 | OMe | O(CH$_2$)$_3$SOEt | |
| 3-161 | OMe | O(CH$_2$)$_3$SO$_2$Et | |
| 3-162 | OMe | 1,4-dioxan-2-ylmethoxy | |
| 3-163 | OMe | 1,3-dioxolan-2-ylmethoxy | |
| 3-164 | OMe | tetrahydrofuran-2-yl-methoxy | |
| 3-165 | OMe | OCH$_2$(CO)NMe$_2$ | |
| 3-166 | OMe | O(CH$_2$)$_2$NHSO$_2$Me | |
| 3-167 | OMe | 4,5-dihydro-3-isoxazolyl | |
| 3-168 | OMe | H | |
| 3-169 | OMe | Me | |
| 3-170 | OMe | (2,2,2-trifluoroethoxy)methyl | |
| 3-171 | OMe | (RS)-tetrahydro-2-furylmethoxymethyl | |

TABLE 4

Compounds according to the invention of the general formula (I) in which Z is $Z^1$, B is N and R is a 2-methoxyethyl group and W is hydrogen and A is CY.

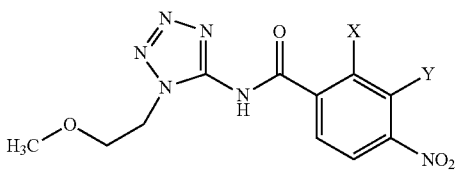

| No. | X | Y | Physical data |
|---|---|---|---|
| 4-1 | Br | OMe | |
| 4-2 | Br | OEt | |
| 4-3 | Br | OPr | |
| 4-4 | Br | O-i-Pr | |
| 4-5 | Br | cyclopropylmethoxy | |
| 4-6 | Br | 2-fluoroethoxy | |
| 4-7 | Br | 2,2-difluoroethoxy | |
| 4-8 | Br | 2,2,2-trifluoroethoxy | |
| 4-9 | Br | OCHF$_2$ | |
| 4-10 | Br | OCH$_2$F | |
| 4-11 | Br | OCF$_3$ | |
| 4-12 | Br | SO$_2$Me | |
| 4-13 | Br | SOMe | |
| 4-14 | Br | SMe | |
| 4-15 | Br | SO$_2$Et | |
| 4-16 | Br | SOEt | |
| 4-17 | Br | Set | |
| 4-18 | Br | O(CH$_2$)$_2$OMe | |
| 4-19 | Br | O(CH$_2$)$_3$OMe | |
| 4-20 | Br | O(CH$_2$)$_2$OEt | |
| 4-21 | Br | O(CH$_2$)$_3$OEt | |
| 4-22 | Br | O(CH$_2$)$_2$SMe | |
| 4-23 | Br | O(CH$_2$)$_2$SOMe | |
| 4-24 | Br | O(CH$_2$)$_2$SO$_2$Me | |
| 4-25 | Br | O(CH$_2$)$_3$SMe | |

TABLE 4-continued

Compounds according to the invention of the general formula (I) in which Z is $Z^1$, B is N and R is a 2-methoxyethyl group and W is hydrogen and A is CY.

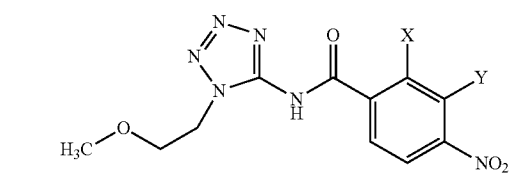

| No. | X | Y | Physical data |
|---|---|---|---|
| 4-26 | Br | O(CH$_2$)$_2$SOMe | |
| 4-27 | Br | O(CH$_2$)$_3$SO$_2$Me | |
| 4-28 | Br | O(CH$_2$)$_2$SEt | |
| 4-29 | Br | O(CH$_2$)$_2$SOEt | |
| 4-30 | Br | O(CH$_2$)$_2$SO$_2$Et | |
| 4-31 | Br | O(CH$_2$)$_3$SEt | |
| 4-32 | Br | O(CH$_2$)$_3$SOEt | |
| 4-33 | Br | O(CH$_2$)$_3$SO$_2$Et | |
| 4-34 | Br | 1,4-dioxan-2-ylmethoxy | |
| 4-35 | Br | 1,3-dioxolan-2-ylmethoxy | |
| 4-36 | Br | tetrahydrofuran-2-yl-methoxy | |
| 4-37 | Br | OCH$_2$(CO)NMe$_2$ | |
| 4-38 | Br | O(CH$_2$)$_2$NHSO$_2$Me | |
| 4-39 | Br | 4,5-dihydro-3-isoxazolyl | |
| 4-40 | Br | H | |
| 4-41 | Br | Me | |
| 4-42 | Br | (2,2,2-trifluoroethoxy)methyl | |
| 4-43 | Br | (RS)-tetrahydro-2-furylmethoxymethyl | |
| 4-44 | Cl | OMe | |
| 4-45 | Cl | OEt | |
| 4-46 | Cl | OPr | |
| 4-47 | Cl | O-i-Pr | |
| 4-48 | Cl | cyclopropylmethoxy | |
| 4-49 | Cl | 2-fluoroethoxy | |
| 4-50 | Cl | 2,2-difluoroethoxy | |
| 4-51 | Cl | 2,2,2-trifluoroethoxy | |
| 4-52 | Cl | OCHF$_2$ | |
| 4-53 | Cl | OCH$_2$F | |
| 4-54 | Cl | OCF$_3$ | |
| 4-55 | Cl | SO$_2$Me | |
| 4-56 | Cl | SOMe | |
| 4-57 | Cl | SMe | |
| 4-58 | Cl | SO$_2$Et | |
| 4-59 | Cl | SOEt | |
| 4-60 | Cl | Set | |
| 4-61 | Cl | O(CH$_2$)$_2$OMe | |
| 4-62 | Cl | O(CH$_2$)$_3$OMe | |
| 4-63 | Cl | O(CH$_2$)$_2$OEt | |
| 4-64 | Cl | O(CH$_2$)$_3$OEt | |
| 4-65 | Cl | O(CH$_2$)$_2$SMe | |
| 4-66 | Cl | O(CH$_2$)$_2$SOMe | |
| 4-67 | Cl | O(CH$_2$)$_2$SO$_2$Me | |
| 4-68 | Cl | O(CH$_2$)$_3$SMe | |
| 4-69 | Cl | O(CH$_2$)$_3$SOMe | |
| 4-70 | Cl | O(CH$_2$)$_3$SO$_2$Me | |
| 4-71 | Cl | O(CH$_2$)$_2$SEt | |
| 4-72 | Cl | O(CH$_2$)$_2$SOEt | |
| 4-73 | Cl | O(CH$_2$)$_2$SO$_2$Et | |
| 4-74 | Cl | O(CH$_2$)$_3$SEt | |
| 4-75 | Cl | O(CH$_2$)$_3$SOEt | |
| 4-76 | Cl | O(CH$_2$)$_3$SO$_2$Et | |
| 4-77 | Cl | 1,4-dioxan-2-ylmethoxy | |
| 4-78 | Cl | 1,3-dioxolan-2-ylmethoxy | |
| 4-79 | Cl | tetrahydrofuran-2-yl-methoxy | |
| 4-80 | Cl | OCH$_2$(CO)NMe$_2$ | |
| 4-81 | Cl | O(CH$_2$)$_2$NHSO$_2$Me | |
| 4-82 | Cl | 4,5-dihydro-3-isoxazolyl | |
| 4-83 | Cl | H | |
| 4-84 | Cl | Me | |
| 4-85 | Cl | (2,2,2-trifluoroethoxy)methyl | |
| 4-86 | Cl | (RS)-tetrahydro-2-furylmethoxymethyl | |
| 4-87 | Me | OMe | |
| 4-88 | Me | OEt | |
| 4-89 | Me | OPr | |
| 4-90 | Me | O-i-Pr | |

TABLE 4-continued

Compounds according to the invention of the general formula (I) in which Z is $Z^1$, B is N and R is a 2-methoxyethyl group and W is hydrogen and A is CY.

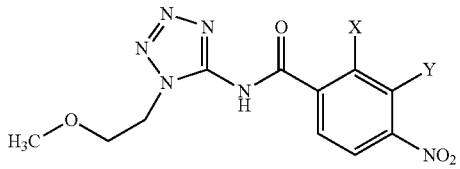

| No. | X | Y | Physical data |
|---|---|---|---|
| 4-91 | Me | cyclopropylmethoxy | |
| 4-92 | Me | 2-fluoroethoxy | |
| 4-93 | Me | 2,2-difluoroethoxy | |
| 4-94 | Me | 2,2,2-trifluoroethoxy | |
| 4-95 | Me | $OCHF_2$ | |
| 4-96 | Me | $OCH_2F$ | |
| 4-97 | Me | $OCF_3$ | |
| 4-98 | Me | $SO_2Me$ | |
| 4-99 | Me | SOMe | |
| 4-100 | Me | SMe | |
| 4-101 | Me | $SO_2Et$ | |
| 4-102 | Me | SOEt | |
| 4-103 | Me | SEt | |
| 4-104 | Me | $O(CH_2)_2OMe$ | |
| 4-105 | Me | $O(CH_2)_3OMe$ | |
| 4-106 | Me | $O(CH_2)_2OEt$ | |
| 4-107 | Me | $O(CH_2)_3OEt$ | |
| 4-108 | Me | $O(CH_2)_2SMe$ | |
| 4-109 | Me | $O(CH_2)_2SOMe$ | |
| 4-110 | Me | $O(CH_2)_2SO_2Me$ | |
| 4-111 | Me | $O(CH_2)_3SMe$ | |
| 4-112 | Me | $O(CH_2)_3SOMe$ | |
| 4-113 | Me | $O(CH_2)_3SO_2Me$ | |
| 4-114 | Me | $O(CH_2)_2SEt$ | |
| 4-115 | Me | $O(CH_2)_2SOEt$ | |
| 4-116 | Me | $O(CH_2)_2SO_2Et$ | |
| 4-117 | Me | $O(CH_2)_3SEt$ | |
| 4-118 | Me | $O(CH_2)_3SOEt$ | |
| 4-119 | Me | $O(CH_2)_3SO_2Et$ | |
| 4-120 | Me | 1,4-dioxan-2-ylmethoxy | |
| 4-121 | Me | 1,3-dioxolan-2-ylmethoxy | |
| 4-122 | Me | tetrahydrofuran-2-yl-methoxy | |
| 4-123 | Me | $OCH_2(CO)NMe_2$ | |
| 4-124 | Me | $O(CH_2)_2NHSO_2Me$ | |
| 4-125 | Me | 4,5-dihydro-3-isoxazolyl | |
| 4-126 | Me | H | |
| 4-127 | Me | Me | |
| 4-128 | Me | (2,2,2-trifluoroethoxy)methyl | |
| 4-129 | Me | (RS)-tetrahydro-2-furylmethoxymethyl | |
| 4-130 | OMe | OMe | |
| 4-131 | OMe | OEt | |
| 4-132 | OMe | OPr | |
| 4-133 | OMe | O-i-Pr | |
| 4-134 | OMe | cyclopropylmethoxy | |
| 4-135 | OMe | 2-fluoroethoxy | |
| 4-136 | OMe | 2,2-difluoroethoxy | |
| 4-137 | OMe | 2,2,2-trifluoroethoxy | |
| 4-138 | OMe | $OCHF_2$ | |
| 4-139 | OMe | $OCH_2F$ | |
| 4-140 | OMe | $OCF_3$ | |
| 4-141 | OMe | $SO_2Me$ | |
| 4-142 | OMe | SOMe | |
| 4-143 | OMe | SMe | |
| 4-144 | OMe | $SO_2Et$ | |
| 4-145 | OMe | SOEt | |
| 4-146 | OMe | SEt | |
| 4-147 | OMe | $O(CH_2)_2OMe$ | |
| 4-148 | OMe | $O(CH_2)_3OMe$ | |
| 4-149 | OMe | $O(CH_2)_2OEt$ | |
| 4-150 | OMe | $O(CH_2)_3OEt$ | |
| 4-151 | OMe | $O(CH_2)_2SMe$ | |
| 4-152 | OMe | $O(CH_2)_2SOMe$ | |
| 4-153 | OMe | $O(CH_2)_2SO_2Me$ | |
| 4-154 | OMe | $O(CH_2)_3SMe$ | |
| 4-155 | OMe | $O(CH_2)_3SOMe$ | |

TABLE 4-continued

Compounds according to the invention of the general formula (I) in which Z is $Z^1$, B is N and R is a 2-methoxyethyl group and W is hydrogen and A is CY.

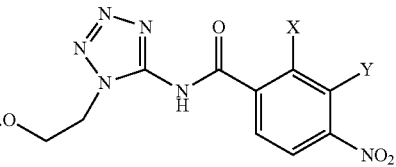

| No. | X | Y | Physical data |
|---|---|---|---|
| 4-156 | OMe | $O(CH_2)_3SO_2Me$ | |
| 4-157 | OMe | $O(CH_2)_2SEt$ | |
| 4-158 | OMe | $O(CH_2)_2SOEt$ | |
| 4-159 | OMe | $O(CH_2)_2SO_2Et$ | |
| 4-160 | OMe | $O(CH_2)_3SEt$ | |
| 4-161 | OMe | $O(CH_2)_3SOEt$ | |
| 4-162 | OMe | $O(CH_2)_3SO_2Et$ | |
| 4-163 | OMe | 1,4-dioxan-2-ylmethoxy | |
| 4-164 | OMe | 1,3-dioxolan-2-ylmethoxy | |
| 4-165 | OMe | tetrahydrofuran-2-yl-methoxy | |
| 4-166 | OMe | $OCH_2(CO)NMe_2$ | |
| 4-167 | OMe | $O(CH_2)_2NHSO_2Me$ | |
| 4-168 | OMe | 4,5-dihydro-3-isoxazolyl | |
| 4-169 | OMe | H | |
| 4-170 | OMe | Me | |
| 4-171 | OMe | (2,2,2-trifluoroethoxy)methyl | |
| 4-172 | OMe | (RS)-tetrahydro-2-furylmethoxymethyl | |

TABLE 5

Compounds according to the invention of the general formula (I) in which Z is $Z^1$, B is CH and R is a methyl group and W is hydrogen and A is CY.

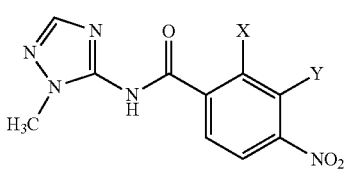

| No. | X | Y | Physical data |
|---|---|---|---|
| 5-1 | Br | OMe | |
| 5-2 | Br | OEt | |
| 5-3 | Br | OPr | |
| 5-4 | Br | O-i-Pr | |
| 5-5 | Br | cyclopropylmethoxy | |
| 5-6 | Br | 2-fluoroethoxy | |
| 5-7 | Br | 2,2-difluoroethoxy | |
| 5-8 | Br | 2,2,2-trifluoroethoxy | |
| 5-9 | Br | $OCHF_2$ | |
| 5-10 | Br | $OCH_2F$ | |
| 5-11 | Br | $OCF_3$ | |
| 5-12 | Br | $SO_2Me$ | |
| 5-13 | Br | SOMe | |
| 5-14 | Br | SMe | |
| 5-15 | Br | $SO_2Et$ | |
| 5-16 | Br | SOEt | |
| 5-17 | Br | SEt | |
| 5-18 | Br | $O(CH_2)_2OMe$ | |
| 5-19 | Br | $O(CH_2)_3OMe$ | 1H NMR, CDCl3, 400 MHz: 7.81 (d, 1H), 7.74 (s, 1H), 7.47 (d, 1H), 4.26 (t, 2H), 3.89 (s, 3H), 3.60 (t, 2H), 3.38 (s, 3H), 2.13 (quin, 2H) |
| 5-20 | Br | $O(CH_2)_2OEt$ | |
| 5-21 | Br | $O(CH_2)_3OEt$ | |
| 5-22 | Br | $O(CH_2)_2SMe$ | |
| 5-23 | Br | $O(CH_2)_2SOMe$ | |
| 5-24 | Br | $O(CH_2)_2SO_2Me$ | |

TABLE 5-continued

Compounds according to the invention of the general formula (I) in which Z is $Z^1$, B is CH and R is a methyl group and W is hydrogen and A is CY.

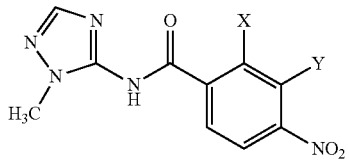

| No. | X | Y | Physical data |
|---|---|---|---|
| 5-25 | Br | O(CH$_2$)$_3$SMe | |
| 5-26 | Br | O(CH$_2$)$_3$SOMe | |
| 5-27 | Br | O(CH$_2$)$_3$SO$_2$Me | |
| 5-28 | Br | O(CH$_2$)$_2$SEt | |
| 5-29 | Br | O(CH$_2$)$_2$SOEt | |
| 5-30 | Br | O(CH$_2$)$_2$SO$_2$Et | |
| 5-31 | Br | O(CH$_2$)$_3$SEt | |
| 5-32 | Br | O(CH$_2$)$_3$SOEt | |
| 5-33 | Br | O(CH$_2$)$_3$SO$_2$Et | |
| 5-34 | Br | 1,4-dioxan-2-ylmethoxy | |
| 5-35 | Br | 1,3-dioxolan-2-ylmethoxy | |
| 5-36 | Br | tetrahydrofuran-2-yl-methoxy | |
| 5-37 | Br | OCH$_2$(CO)NMe$_2$ | |
| 5-38 | Br | O(CH$_2$)$_2$NHSO$_2$Me | |
| 5-39 | Br | 4,5-dihydro-3-isoxazolyl | |
| 5-40 | Br | H | |
| 5-41 | Br | Me | |
| 5-42 | Br | (2,2,2-trifluoroethoxy)methyl | |
| 5-43 | Br | (RS)-tetrahydro-2-furylmethoxymethyl | |
| 5-44 | Cl | OMe | |
| 5-45 | Cl | OEt | |
| 5-46 | Cl | OPr | |
| 5-47 | Cl | O-i-Pr | |
| 5-48 | Cl | cyclopropylmethoxy | |
| 5-49 | Cl | 2-fluoroethoxy | |
| 5-50 | Cl | 2,2-difluoroethoxy | |
| 5-51 | Cl | 2,2,2-trifluoroethoxy | |
| 5-52 | Cl | OCHF$_2$ | |
| 5-53 | Cl | OCH$_2$F | |
| 5-54 | Cl | OCF$_3$ | |
| 5-55 | Cl | SO$_2$Me | |
| 5-56 | Cl | SOMe | |
| 5-57 | Cl | SMe | |
| 5-58 | Cl | SO$_2$Et | |
| 5-59 | Cl | SOEt | |
| 5-60 | Cl | Set | |
| 5-61 | Cl | O(CH$_2$)$_2$OMe | |
| 5-62 | Cl | O(CH$_2$)$_3$OMe | |
| 5-63 | Cl | O(CH$_2$)$_2$OEt | |
| 5-64 | Cl | O(CH$_2$)$_3$OEt | |
| 5-65 | Cl | O(CH$_2$)$_2$SMe | |
| 5-66 | Cl | O(CH$_2$)$_2$SOMe | |
| 5-67 | Cl | O(CH$_2$)$_2$SO$_2$Me | |
| 5-68 | Cl | O(CH$_2$)$_3$SMe | |
| 5-69 | Cl | O(CH$_2$)$_3$SOMe | |
| 5-70 | Cl | O(CH$_2$)$_3$SO$_2$Me | |
| 5-71 | Cl | O(CH$_2$)$_2$SEt | |
| 5-72 | Cl | O(CH$_2$)$_2$SOEt | |
| 5-73 | Cl | O(CH$_2$)$_2$SO$_2$Et | |
| 5-74 | Cl | O(CH$_2$)$_3$SEt | |
| 5-75 | Cl | O(CH$_2$)$_3$SOEt | |
| 5-76 | Cl | O(CH$_2$)$_3$SO$_2$Et | |
| 5-77 | Cl | 1,4-dioxan-2-ylmethoxy | |
| 5-78 | Cl | 1,3-dioxolan-2-ylmethoxy | |
| 5-79 | Cl | tetrahydrofuran-2-yl-methoxy | |
| 5-80 | Cl | OCH$_2$(CO)NMe$_2$ | |
| 5-81 | Cl | O(CH$_2$)$_2$NHSO$_2$Me | |
| 5-82 | Cl | 4,5-dihydro-3-isoxazolyl | |
| 5-83 | Cl | H | 1H NMR, DMSO-d6, 400 MHz: 11.49 (bs, 1H), 8.43 (s, 1H), 8.31 (d, 1H), 8.00 (d, 1H), 7.92 (s, 1H), 3.79 (s, 3H) |
| 5-84 | Cl | Me | |
| 5-85 | Cl | (2,2,2-trifluoroethoxy)methyl | |

TABLE 5-continued

Compounds according to the invention of the general formula (I) in which Z is $Z^1$, B is CH and R is a methyl group and W is hydrogen and A is CY.

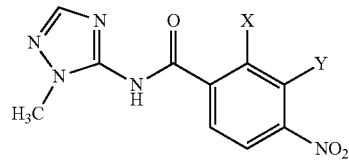

| No. | X | Y | Physical data |
|---|---|---|---|
| 5-86 | Cl | (RS)-tetrahydro-2-furylmethoxymethyl | |
| 5-87 | Me | OMe | |
| 5-88 | Me | OEt | |
| 5-89 | Me | OPr | |
| 5-90 | Me | O-i-Pr | |
| 5-91 | Me | cyclopropylmethoxy | |
| 5-92 | Me | 2-fluoroethoxy | |
| 5-93 | Me | 2,2-difluoroethoxy | |
| 5-94 | Me | 2,2,2-trifluoroethoxy | |
| 5-95 | Me | OCHF$_2$ | |
| 5-96 | Me | OCH$_2$F | |
| 5-97 | Me | OCF$_3$ | |
| 5-98 | Me | SO$_2$Me | |
| 5-99 | Me | SOMe | |
| 5-100 | Me | SMe | |
| 5-101 | Me | SO$_2$Et | |
| 5-102 | Me | SOEt | |
| 5-103 | Me | Set | |
| 5-104 | Me | O(CH$_2$)$_2$OMe | |
| 5-105 | Me | O(CH$_2$)$_3$OMe | |
| 5-106 | Me | O(CH$_2$)$_2$OEt | |
| 5-107 | Me | O(CH$_2$)$_3$OEt | |
| 5-108 | Me | O(CH$_2$)$_2$SMe | |
| 5-109 | Me | O(CH$_2$)$_2$SOMe | |
| 5-110 | Me | O(CH$_2$)$_2$SO$_2$Me | |
| 5-111 | Me | O(CH$_2$)$_3$SMe | |
| 5-112 | Me | O(CH$_2$)$_3$SOMe | |
| 5-113 | Me | O(CH$_2$)$_3$SO$_2$Me | |
| 5-114 | Me | O(CH$_2$)$_2$SEt | |
| 5-115 | Me | O(CH$_2$)$_2$SOEt | |
| 5-116 | Me | O(CH$_2$)$_2$SO$_2$Et | |
| 5-117 | Me | O(CH$_2$)$_3$SEt | |
| 5-118 | Me | O(CH$_2$)$_3$SOEt | |
| 5-119 | Me | O(CH$_2$)$_3$SO$_2$Et | |
| 5-120 | Me | 1,4-dioxan-2-ylmethoxy | |
| 5-121 | Me | 1,3-dioxolan-2-ylmethoxy | |
| 5-122 | Me | tetrahydrofuran-2-yl-methoxy | |
| 5-123 | Me | OCH$_2$(CO)NMe$_2$ | |
| 5-124 | Me | O(CH$_2$)$_2$NHSO$_2$Me | |
| 5-125 | Me | 4,5-dihydro-3-isoxazolyl | |
| 5-126 | Me | H | |
| 5-127 | Me | Me | |
| 5-128 | Me | (2,2,2-trifluoroethoxy)methyl | |
| 5-129 | Me | (RS)-tetrahydro-2-furylmethoxymethyl | |
| 5-130 | OMe | OMe | |
| 5-131 | OMe | OEt | |
| 5-132 | OMe | OPr | |
| 5-133 | OMe | O-i-Pr | |
| 5-134 | OMe | cyclopropylmethoxy | |
| 5-135 | OMe | 2-fluoroethoxy | |
| 5-136 | OMe | 2,2-difluoroethoxy | |
| 5-137 | OMe | 2,2,2-trifluoroethoxy | |
| 5-138 | OMe | OCHF$_2$ | |
| 5-139 | OMe | OCH$_2$F | |
| 5-140 | OMe | OCF$_3$ | |
| 5-141 | OMe | SO$_2$Me | |
| 5-142 | OMe | SOMe | |
| 5-143 | OMe | SMe | |
| 5-144 | OMe | SO$_2$Et | |
| 5-145 | OMe | SOEt | |
| 5-146 | OMe | Set | |
| 5-147 | OMe | O(CH$_2$)$_2$OMe | |
| 5-148 | OMe | O(CH$_2$)$_3$OMe | |
| 5-149 | OMe | O(CH$_2$)$_2$OEt | |

TABLE 5-continued

Compounds according to the invention of the general formula (I) in which Z is $Z^1$, B is CH and R is a methyl group and W is hydrogen and A is CY.

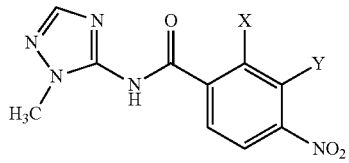

| No. | X | Y | Physical data |
|---|---|---|---|
| 5-150 | OMe | O(CH$_2$)$_3$OEt | |
| 5-151 | OMe | O(CH$_2$)$_2$SMe | |
| 5-152 | OMe | O(CH$_2$)$_2$SOMe | |
| 5-153 | OMe | O(CH$_2$)$_2$SO$_2$Me | |
| 5-154 | OMe | O(CH$_2$)$_3$SMe | |
| 5-155 | OMe | O(CH$_2$)$_3$SOMe | |
| 5-156 | OMe | O(CH$_2$)$_3$SO$_2$Me | |
| 5-157 | OMe | O(CH$_2$)$_2$SEt | |
| 5-158 | OMe | O(CH$_2$)$_2$SOEt | |
| 5-159 | OMe | O(CH$_2$)$_2$SO$_2$Et | |
| 5-160 | OMe | O(CH$_2$)$_3$SEt | |
| 5-161 | OMe | O(CH$_2$)$_3$SOEt | |
| 5-162 | OMe | O(CH$_2$)$_3$SO$_2$Et | |
| 5-163 | OMe | 1,4-dioxan-2-ylmethoxy | |
| 5-164 | OMe | 1,3-dioxolan-2-ylmethoxy | |
| 5-165 | OMe | tetrahydrofuran-2-yl-methoxy | |
| 5-166 | OMe | OCH$_2$(CO)NMe$_2$ | |
| 5-167 | OMe | O(CH$_2$)$_2$NHSO$_2$Me | |
| 5-168 | OMe | 4,5-dihydro-3-isoxazolyl | |
| 5-169 | OMe | H | |
| 5-170 | OMe | Me | |
| 5-171 | OMe | (2,2,2-trifluoroethoxy)methyl | |
| 5-172 | OMe | (RS)-tetrahydro-2-furylmethoxymethyl | |

TABLE 6

Compounds according to the invention of the general formula (I) in which Z is $Z^2$, and R' is a methyl group and W is hydrogen and A is CY.

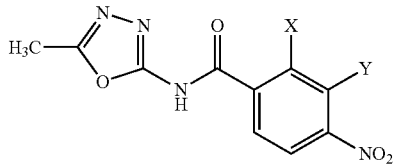

| No. | X | Y | Physical data |
|---|---|---|---|
| 6-1 | Br | OMe | |
| 6-2 | Br | OEt | |
| 6-3 | Br | OPr | |
| 6-4 | Br | O-i-Pr | |
| 6-5 | Br | cyclopropylmethoxy | |
| 6-6 | Br | 2-fluoroethoxy | |
| 6-7 | Br | 2,2-difluoroethoxy | |
| 6-8 | Br | 2,2,2-trifluoroethoxy | |
| 6-9 | Br | OCHF$_2$ | |
| 6-10 | Br | OCH$_2$F | |
| 6-11 | Br | OCF$_3$ | |
| 6-12 | Br | SO$_2$Me | |
| 6-13 | Br | SOMe | |
| 6-14 | Br | SMe | |
| 6-15 | Br | SO$_2$Et | |
| 6-16 | Br | SOEt | |
| 6-17 | Br | SEt | |
| 6-18 | Br | O(CH$_2$)$_2$OMe | |
| 6-19 | Br | O(CH$_2$)$_3$OMe | |
| 6-20 | Br | O(CH$_2$)$_2$OEt | |
| 6-21 | Br | O(CH$_2$)$_3$OEt | |
| 6-22 | Br | O(CH$_2$)$_2$SMe | |
| 6-23 | Br | O(CH$_2$)$_2$SOMe | |

TABLE 6-continued

Compounds according to the invention of the general formula (I) in which Z is $Z^2$, and R' is a methyl group and W is hydrogen and A is CY.

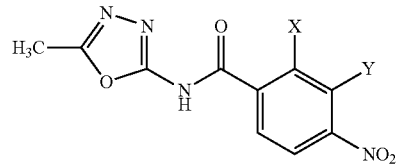

| No. | X | Y | Physical data |
|---|---|---|---|
| 6-24 | Br | O(CH$_2$)$_2$SO$_2$Me | |
| 6-25 | Br | O(CH$_2$)$_3$SMe | |
| 6-26 | Br | O(CH$_2$)$_3$SOMe | |
| 6-27 | Br | O(CH$_2$)$_3$SO$_2$Me | |
| 6-28 | Br | O(CH$_2$)$_2$SEt | |
| 6-29 | Br | O(CH$_2$)$_2$SOEt | |
| 6-30 | Br | O(CH$_2$)$_2$SO$_2$Et | |
| 6-31 | Br | O(CH$_2$)$_3$SEt | |
| 6-32 | Br | O(CH$_2$)$_3$SOEt | |
| 6-33 | Br | O(CH$_2$)$_3$SO$_2$Et | |
| 6-34 | Br | 1,4-dioxan-2-ylmethoxy | |
| 6-35 | Br | 1,3-dioxolan-2-ylmethoxy | |
| 6-36 | Br | tetrahydrofuran-2-yl-methoxy | |
| 6-37 | Br | OCH$_2$(CO)NMe$_2$ | |
| 6-38 | Br | O(CH$_2$)$_2$NHSO$_2$Me | |
| 6-39 | Br | 4,5-dihydro-3-isoxazolyl | |
| 6-40 | Br | H | |
| 6-41 | Br | Me | |
| 6-42 | Br | (2,2,2-trifluoroethoxy)methyl | |
| 6-43 | Br | (RS)-tetrahydro-2-furylmethoxymethyl | |
| 6-44 | Cl | OMe | |
| 6-45 | Cl | OEt | |
| 6-46 | Cl | OPr | |
| 6-47 | Cl | O-i-Pr | |
| 6-48 | Cl | cyclopropylmethoxy | |
| 6-49 | Cl | 2-fluoroethoxy | |
| 6-50 | Cl | 2,2-difluoroethoxy | |
| 6-51 | Cl | 2,2,2-trifluoroethoxy | |
| 6-52 | Cl | OCHF$_2$ | |
| 6-53 | Cl | OCH$_2$F | |
| 6-54 | Cl | OCF$_3$ | |
| 6-55 | Cl | SO$_2$Me | |
| 6-56 | Cl | SOMe | |
| 6-57 | Cl | SMe | |
| 6-58 | Cl | SO$_2$Et | |
| 6-59 | Cl | SOEt | |
| 6-60 | Cl | SEt | |
| 6-61 | Cl | O(CH$_2$)$_2$OMe | |
| 6-62 | Cl | O(CH$_2$)$_3$OMe | |
| 6-63 | Cl | O(CH$_2$)$_2$OEt | |
| 6-64 | Cl | O(CH$_2$)$_3$OEt | |
| 6-65 | Cl | O(CH$_2$)$_2$SMe | |
| 6-66 | Cl | O(CH$_2$)$_2$SOMe | |
| 6-67 | Cl | O(CH$_2$)$_2$SO$_2$Me | |
| 6-68 | Cl | O(CH$_2$)$_3$SMe | |
| 6-69 | Cl | O(CH$_2$)$_3$SOMe | |
| 6-70 | Cl | O(CH$_2$)$_3$SO$_2$Me | |
| 6-71 | Cl | O(CH$_2$)$_2$SEt | |
| 6-72 | Cl | O(CH$_2$)$_2$SOEt | |
| 6-73 | Cl | O(CH$_2$)$_2$SO$_2$Et | |
| 6-74 | Cl | O(CH$_2$)$_3$SEt | |
| 6-75 | Cl | O(CH$_2$)$_3$SOEt | |
| 6-76 | Cl | O(CH$_2$)$_3$SO$_2$Et | |
| 6-77 | Cl | 1,4-dioxan-2-ylmethoxy | |
| 6-78 | Cl | 1,3-dioxolan-2-ylmethoxy | |
| 6-79 | Cl | tetrahydrofuran-2-yl-methoxy | |
| 6-80 | Cl | OCH$_2$(CO)NMe$_2$ | |
| 6-81 | Cl | O(CH$_2$)$_2$NHSO$_2$Me | |
| 6-82 | Cl | 4,5-dihydro-3-isoxazolyl | |
| 6-83 | Cl | H | |
| 6-84 | Cl | Me | |
| 6-85 | Cl | (2,2,2-trifluoroethoxy)methyl | |
| 6-86 | Cl | (RS)-tetrahydro-2-furylmethoxymethyl | |
| 6-87 | Me | OMe | |
| 6-88 | Me | OEt | |
| 6-89 | Me | OPr | |

TABLE 6-continued

Compounds according to the invention of the general formula (I) in which Z is $Z^2$, and R' is a methyl group and W is hydrogen and A is CY.

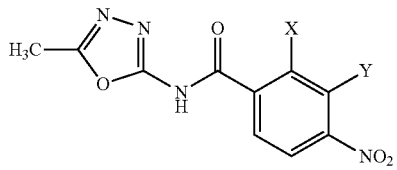

| No. | X | Y | Physical data |
|---|---|---|---|
| 6-90 | Me | O-i-Pr | |
| 6-91 | Me | cyclopropylmethoxy | |
| 6-92 | Me | 2-fluoroethoxy | |
| 6-93 | Me | 2,2-difluoroethoxy | |
| 6-94 | Me | 2,2,2-trifluoroethoxy | |
| 6-95 | Me | $OCHF_2$ | |
| 6-96 | Me | $OCH_2F$ | |
| 6-97 | Me | $OCF_3$ | |
| 6-98 | Me | $SO_2Me$ | |
| 6-99 | Me | SOMe | |
| 6-100 | Me | SMe | |
| 6-101 | Me | $SO_2Et$ | |
| 6-102 | Me | SOEt | |
| 6-103 | Me | SEt | |
| 6-104 | Me | $O(CH_2)_2OMe$ | |
| 6-105 | Me | $O(CH_2)_3OMe$ | |
| 6-106 | Me | $O(CH_2)_2OEt$ | |
| 6-107 | Me | $O(CH_2)_3OEt$ | |
| 6-108 | Me | $O(CH_2)_2SMe$ | |
| 6-109 | Me | $O(CH_2)_2SOMe$ | |
| 6-110 | Me | $O(CH_2)_2SO_2Me$ | |
| 6-111 | Me | $O(CH_2)_3SMe$ | |
| 6-112 | Me | $O(CH_2)_3SOMe$ | |
| 6-113 | Me | $O(CH_2)_3SO_2Me$ | |
| 6-114 | Me | $O(CH_2)_2SEt$ | |
| 6-115 | Me | $O(CH_2)_2SOEt$ | |
| 6-116 | Me | $O(CH_2)_2SO_2Et$ | |
| 6-117 | Me | $O(CH_2)_3SEt$ | |
| 6-118 | Me | $O(CH_2)_3SOEt$ | |
| 6-119 | Me | $O(CH_2)_3SO_2Et$ | |
| 6-120 | Me | 1,4-dioxan-2-ylmethoxy | |
| 6-121 | Me | 1,3-dioxolan-2-ylmethoxy | |
| 6-122 | Me | tetrahydrofuran-2-yl-methoxy | |
| 6-123 | Me | $OCH_2(CO)NMe_2$ | |
| 6-124 | Me | $O(CH_2)_2NHSO_2Me$ | |
| 6-125 | Me | 4,5-dihydro-3-isoxazolyl | |
| 6-126 | Me | H | |
| 6-127 | Me | Me | |
| 6-128 | Me | (2,2,2-trifluoroethoxy)methyl | |
| 6-129 | Me | (RS)-tetrahydro-2-furylmethoxymethyl | |
| 6-130 | OMe | OMe | |
| 6-131 | OMe | OEt | |
| 6-132 | OMe | OPr | |
| 6-133 | OMe | O-i-Pr | |
| 6-134 | OMe | cyclopropylmethoxy | |
| 6-135 | OMe | 2-fluoroethoxy | |
| 6-136 | OMe | 2,2-difluoroethoxy | |
| 6-137 | OMe | 2,2,2-trifluoroethoxy | |
| 6-138 | OMe | $OCHF_2$ | |
| 6-139 | OMe | $OCH_2F$ | |
| 6-140 | OMe | $OCF_3$ | |
| 6-141 | OMe | $SO_2Me$ | |
| 6-142 | OMe | SOMe | |
| 6-143 | OMe | SMe | |
| 6-144 | OMe | $SO_2Et$ | |
| 6-145 | OMe | SOEt | |
| 6-146 | OMe | SEt | |
| 6-147 | OMe | $O(CH_2)_2OMe$ | |
| 6-148 | OMe | $O(CH_2)_3OMe$ | |
| 6-149 | OMe | $O(CH_2)_2OEt$ | |
| 6-150 | OMe | $O(CH_2)_3OEt$ | |
| 6-151 | OMe | $O(CH_2)_2SMe$ | |
| 6-152 | OMe | $O(CH_2)_2SOMe$ | |
| 6-153 | OMe | $O(CH_2)_2SO_2Me$ | |
| 6-154 | OMe | $O(CH_2)_3SMe$ | |
| 6-155 | OMe | $O(CH_2)_3SOMe$ | |

TABLE 6-continued

Compounds according to the invention of the general formula (I) in which Z is $Z^2$, and R' is a methyl group and W is hydrogen and A is CY.

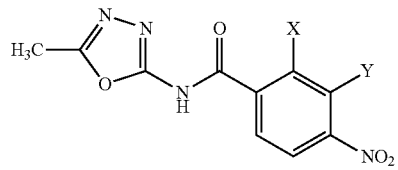

| No. | X | Y | Physical data |
|---|---|---|---|
| 6-156 | OMe | $O(CH_2)_3SO_2Me$ | |
| 6-157 | OMe | $O(CH_2)_2SEt$ | |
| 6-158 | OMe | $O(CH_2)_2SOEt$ | |
| 6-159 | OMe | $O(CH_2)_2SO_2Et$ | |
| 6-160 | OMe | $O(CH_2)_3SEt$ | |
| 6-161 | OMe | $O(CH_2)_3SOEt$ | |
| 6-162 | OMe | $O(CH_2)_3SO_2Et$ | |
| 6-163 | OMe | 1,4-dioxan-2-ylmethoxy | |
| 6-164 | OMe | 1,3-dioxolan-2-ylmethoxy | |
| 6-165 | OMe | tetrahydrofuran-2-yl-methoxy | |
| 6-166 | OMe | $OCH_2(CO)NMe_2$ | |
| 6-167 | OMe | $O(CH_2)_2NHSO_2Me$ | |
| 6-168 | OMe | 4,5-dihydro-3-isoxazolyl | |
| 6-169 | OMe | H | |
| 6-170 | OMe | Me | |
| 6-171 | OMe | (2,2,2-trifluoroethoxy)methyl | |
| 6-172 | OMe | (RS)-tetrahydro-2-furylmethoxymethyl | |

TABLE 7

Compounds according to the invention of the general formula (I) in which Z is $Z^1$, B is N and R is a methyl group and W is hydrogen and A is N.

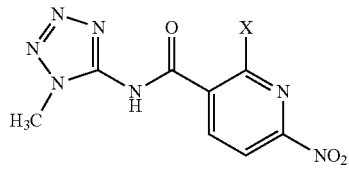

| No. | X | Physical data |
|---|---|---|
| 7-1 | Me | |
| 7-2 | Et | |
| 7-3 | OMe | |
| 7-4 | OEt | |
| 7-5 | Cl | |
| 7-6 | Br | |
| 7-7 | $CF_3$ | |
| 7-8 | $CH_2OMe$ | |
| 7-9 | $CH_2OEt$ | |
| 7-10 | $CH_2O(CH_2)_2OMe$ | |
| 7-11 | $CH_2O(CH_2)_2OEt$ | |
| 7-12 | $CH_2O(CH_2)_2SMe$ | |
| 7-13 | $CH_2O(CH_2)_3OMe$ | |
| 7-14 | $CH_2O(CH_2)_3OEt$ | |
| 7-15 | $CH_2O(CH_2)_3SMe$ | |

TABLE 8

Compounds according to the invention of the general formula (I) in the form of the sodium salts, in which Z is $Z^1$, B is N and R is a methyl group and W is hydrogen and A is N.

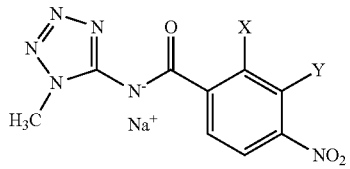

| No. | X | Y | Physical data |
|---|---|---|---|
| 8-1 | Br | OMe | |
| 8-2 | Br | OEt | |
| 8-3 | Br | OPr | |
| 8-4 | Br | O-i-Pr | |
| 8-5 | Br | cyclopropylmethoxy | |
| 8-6 | Br | 2-fluoroethoxy | |
| 8-7 | Br | 2,2-difluoroethoxy | |
| 8-8 | Br | 2,2,2-trifluoroethoxy | |
| 8-9 | Br | $OCHF_2$ | |
| 8-10 | Br | $OCH_2F$ | |
| 8-11 | Br | $OCF_3$ | |
| 8-12 | Br | $SO_2Me$ | |
| 8-13 | Br | SOMe | |
| 8-14 | Br | SMe | |
| 8-15 | Br | $SO_2Et$ | |
| 8-16 | Br | SOEt | |
| 8-17 | Br | SEt | |
| 8-18 | Br | $O(CH_2)_2OMe$ | |
| 8-19 | Br | $O(CH_2)_3OMe$ | |
| 8-20 | Br | $O(CH_2)_2OEt$ | |
| 8-21 | Br | $O(CH_2)_3OEt$ | |
| 8-22 | Br | $O(CH_2)_2SMe$ | |
| 8-23 | Br | $O(CH_2)_2SOMe$ | |
| 8-24 | Br | $O(CH_2)_2SO_2Me$ | |
| 8-25 | Br | $O(CH_2)_3SMe$ | |
| 8-26 | Br | $O(CH_2)_3SOMe$ | |
| 8-27 | Br | $O(CH_2)_3SO_2Me$ | |
| 8-28 | Br | $O(CH_2)_2SEt$ | |
| 8-29 | Br | $O(CH_2)_2SOEt$ | |
| 8-30 | Br | $O(CH_2)_2SO_2Et$ | |
| 8-31 | Br | $O(CH_2)_3SEt$ | |
| 8-32 | Br | $O(CH_2)_3SOEt$ | |
| 8-33 | Br | $O(CH_2)_3SO_2Et$ | |
| 8-34 | Br | 1,5-dioxan-2-ylmethoxy | |
| 8-35 | Br | 1,3-dioxolan-2-ylmethoxy | |
| 8-36 | Br | tetrahydrofuran-2-yl-methoxy | |
| 8-37 | Br | $OCH_2(CO)NMe_2$ | |
| 8-38 | Br | $O(CH_2)_2NHSO_2Me$ | |
| 8-39 | Br | 4,5-dihydro-3-isoxazolyl | |
| 8-40 | Br | H | |
| 8-41 | Br | Me | |
| 8-42 | Br | (2,2,2-trifluoroethoxy)methyl | |
| 8-43 | Br | (RS)-tetrahydro-2-furylmethoxymethyl | |
| 8-44 | Cl | OMe | |
| 8-45 | Cl | OEt | |
| 8-46 | Cl | OPr | |
| 8-47 | Cl | O-i-Pr | |
| 8-48 | Cl | cyclopropylmethoxy | |
| 8-49 | Cl | 2-fluoroethoxy | |
| 8-50 | Cl | 2,2-difluoroethoxy | |
| 8-51 | Cl | 2,2,2-trifluoroethoxy | |
| 8-52 | Cl | $OCHF_2$ | |
| 8-53 | Cl | $OCH_2F$ | |
| 8-54 | Cl | $OCF_3$ | |
| 8-55 | Cl | $SO_2Me$ | |
| 8-56 | Cl | SOMe | |
| 8-57 | Cl | SMe | |
| 8-58 | Cl | $SO_2Et$ | |
| 8-59 | Cl | SOEt | |
| 8-60 | Cl | SEt | |
| 8-61 | Cl | $O(CH_2)_2OMe$ | |
| 8-62 | Cl | $O(CH_2)_3OMe$ | |
| 8-63 | Cl | $O(CH_2)_2OEt$ | |
| 8-64 | Cl | $O(CH_2)_3OEt$ | |
| 8-65 | Cl | $O(CH_2)_2SMe$ | |

TABLE 8-continued

Compounds according to the invention of the general formula (I) in the form of the sodium salts, in which Z is $Z^1$, B is N and R is a methyl group and W is hydrogen and A is N.

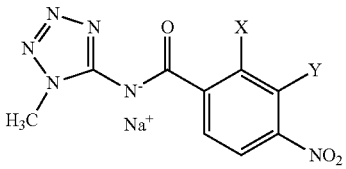

| No. | X | Y | Physical data |
|---|---|---|---|
| 8-66 | Cl | $O(CH_2)_2SOMe$ | |
| 8-67 | Cl | $O(CH_2)_2SO_2Me$ | |
| 8-68 | Cl | $O(CH_2)_3SMe$ | |
| 8-69 | Cl | $O(CH_2)_3SOMe$ | |
| 8-70 | Cl | $O(CH_2)_3SO_2Me$ | |
| 8-71 | Cl | $O(CH_2)_2SEt$ | |
| 8-72 | Cl | $O(CH_2)_2SOEt$ | |
| 8-73 | Cl | $O(CH_2)_2SO_2Et$ | |
| 8-74 | Cl | $O(CH_2)_3SEt$ | |
| 8-75 | Cl | $O(CH_2)_3SOEt$ | |
| 8-76 | Cl | $O(CH_2)_3SO_2Et$ | |
| 8-77 | Cl | 1,5-dioxan-2-ylmethoxy | |
| 8-78 | Cl | 1,3-dioxolan-2-ylmethoxy | |
| 8-79 | Cl | tetrahydrofuran-2-yl-methoxy | |
| 8-80 | Cl | $OCH_2(CO)NMe_2$ | |
| 8-81 | Cl | $O(CH_2)_2NHSO_2Me$ | |
| 8-82 | Cl | 4,5-dihydro-3-isoxazolyl | |
| 8-83 | Cl | H | |
| 8-84 | Cl | Me | |
| 8-85 | Cl | (2,2,2-trifluoroethoxy)methyl | |
| 8-86 | Cl | (RS)-tetrahydro-2-furylmethoxymethyl | |
| 8-87 | Me | OMe | |
| 8-88 | Me | OEt | |
| 8-89 | Me | OPr | |
| 8-90 | Me | O-i-Pr | |
| 8-91 | Me | cyclopropylmethoxy | |
| 8-92 | Me | 2-fluoroethoxy | |
| 8-93 | Me | 2,2-difluoroethoxy | |
| 8-94 | Me | 2,2,2-trifluoroethoxy | |
| 8-95 | Me | $OCHF_2$ | |
| 8-96 | Me | $OCH_2F$ | |
| 8-97 | Me | $OCF_3$ | |
| 8-98 | Me | $SO_2Me$ | |
| 8-99 | Me | SOMe | |
| 8-100 | Me | SMe | |
| 8-101 | Me | $SO_2Et$ | |
| 8-102 | Me | SOEt | |
| 8-103 | Me | SEt | |
| 8-104 | Me | $O(CH_2)_2OMe$ | |
| 8-105 | Me | $O(CH_2)_3OMe$ | |
| 8-106 | Me | $O(CH_2)_2OEt$ | |
| 8-107 | Me | $O(CH_2)_3OEt$ | |
| 8-108 | Me | $O(CH_2)_2SMe$ | |
| 8-109 | Me | $O(CH_2)_2SOMe$ | |
| 8-110 | Me | $O(CH_2)_2SO_2Me$ | |
| 8-111 | Me | $O(CH_2)_3SMe$ | |
| 8-112 | Me | $O(CH_2)_3SOMe$ | |
| 8-113 | Me | $O(CH_2)_3SO_2Me$ | |
| 8-114 | Me | $O(CH_2)_2SEt$ | |
| 8-115 | Me | $O(CH_2)_2SOEt$ | |
| 8-116 | Me | $O(CH_2)_2SO_2Et$ | |
| 8-117 | Me | $O(CH_2)_3SEt$ | |
| 8-118 | Me | $O(CH_2)_3SOEt$ | |
| 8-119 | Me | $O(CH_2)_3SO_2Et$ | |
| 8-120 | Me | 1,4-dioxan-2-ylmethoxy | |
| 8-121 | Me | 1,3-dioxolan-2-ylmethoxy | |
| 8-122 | Me | tetrahydrofuran-2-yl-methoxy | |
| 8-123 | Me | $OCH_2(CO)NMe_2$ | |
| 8-124 | Me | $O(CH_2)_2NHSO_2Me$ | |
| 8-125 | Me | 4,5-dihydro-3-isoxazolyl | |
| 8-126 | Me | H | |
| 8-127 | Me | Me | |
| 8-128 | Me | (2,2,2-trifluoroethoxy)methyl | |
| 8-129 | Me | (RS)-tetrahydro-2-furylmethoxymethyl | |
| 8-130 | OMe | OMe | |

TABLE 8-continued

Compounds according to the invention of the general formula (I) in the form of the sodium salts, in which Z is Z¹, B is N and R is a methyl group and W is hydrogen and A is N.

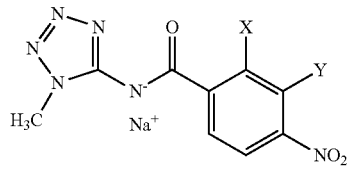

| No. | X | Y | Physical data |
|---|---|---|---|
| 8-131 | OMe | OEt | |
| 8-132 | OMe | OPr | |
| 8-133 | OMe | O-i-Pr | |
| 8-134 | OMe | cyclopropylmethoxy | |
| 8-135 | OMe | 2-fluoroethoxy | |
| 8-136 | OMe | 2,2-difluoroethoxy | |
| 8-137 | OMe | 2,2,2-trifluoroethoxy | |
| 8-138 | OMe | OCHF$_2$ | |
| 8-139 | OMe | OCH$_2$F | |
| 8-140 | OMe | OCF$_3$ | |
| 8-141 | OMe | SO$_2$Me | |
| 8-142 | OMe | SOMe | |
| 8-143 | OMe | SMe | |
| 8-144 | OMe | SO$_2$Et | |
| 8-145 | OMe | SOEt | |
| 8-146 | OMe | Set | |
| 8-147 | OMe | O(CH$_2$)$_2$OMe | |
| 8-148 | OMe | O(CH$_2$)$_3$OMe | |
| 8-149 | OMe | O(CH$_2$)$_2$OEt | |
| 8-150 | OMe | O(CH$_2$)$_3$OEt | |
| 8-151 | OMe | O(CH$_2$)$_2$SMe | |
| 8-152 | OMe | O(CH$_2$)$_2$SOMe | |
| 8-153 | OMe | O(CH$_2$)$_2$SO$_2$Me | |
| 8-154 | OMe | O(CH$_2$)$_3$SMe | |
| 8-155 | OMe | O(CH$_2$)$_3$SOMe | |
| 8-156 | OMe | O(CH$_2$)$_3$SO$_2$Me | |
| 8-157 | OMe | O(CH$_2$)$_2$SEt | |
| 8-158 | OMe | O(CH$_2$)$_2$SOEt | |
| 8-159 | OMe | O(CH$_2$)$_2$SO$_2$Et | |
| 8-160 | OMe | O(CH$_2$)$_3$SEt | |
| 8-161 | OMe | O(CH$_2$)$_3$SOEt | |
| 8-162 | OMe | O(CH$_2$)$_3$SO$_2$Et | |
| 8-163 | OMe | 1,5-dioxan-2-ylmethoxy | |
| 8-164 | OMe | 1,3-dioxolan-2-ylmethoxy | |
| 8-165 | OMe | tetrahydrofuran-2-yl-methoxy | |
| 8-166 | OMe | OCH$_2$(CO)NMe$_2$ | |
| 8-167 | OMe | O(CH$_2$)$_2$NHSO$_2$Me | |
| 8-168 | OMe | 4,5-dihydro-3-isoxazolyl | |
| 8-169 | OMe | H | |
| 8-170 | OMe | Me | |
| 8-171 | OMe | (2,2,2-trifluoroethoxy)methyl | |
| 8-172 | OMe | (RS)-tetrahydro-2-furylmethoxymethyl | |

B. FORMULATION EXAMPLES a) A dusting powder is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
  75 parts by weight of a compound of the formula (I) and/or salts thereof,
  10 parts by weight of calcium lignosulfonate,
  5 parts by weight of sodium laurylsulfate,
  3 parts by weight of polyvinyl alcohol and
  7 parts by weight of kaolin,
  grinding the mixture in a pinned-disk mill and granulating the powder in a fluidized bed by spraying on water as the granulation liquid.

f) Water-dispersible granules are also obtained by homogenizing and precomminuting
  25 parts by weight of a compound of the formula (I) and/or salts thereof,
  5 parts by weight of sodium 2,2'-dinaphthylmethane-6,6'-disulfonate,
  2 parts by weight of sodium oleoylmethyltaurate,
  1 part by weight of polyvinyl alcohol,
  17 parts by weight of calcium carbonate and
  50 parts by weight of water
  in a colloid mill, then grinding the mixture in a bead mill and atomizing and drying the resulting suspension in a spray tower by means of a one-phase nozzle.

C. BIOLOGICAL EXAMPLES

1. Pre-emergence Herbicidal Action Against Weed Plants

Seeds of monocotyledonous and dicotyledonous weed plants and crop plants are placed in wood-fiber pots in sandy loam and covered with soil. The compounds according to the invention, which have been formulated in the form of wettable powders (WP) or as emulsion concentrates (EC) are then applied to the surface of the soil cover in the form of an aqueous suspension or emulsion at a water application rate of (converted) 600 to 800 l/ha, with addition of 0.2% wetting agent. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). Here, for example, compounds No. 1-20, 1-34, 1-61, 1-62, 1-77, 1-78, 2-19, 2-61, 2-62, 2-104, 2-123 and 5-19 have in each case an at least 80% activity against *Matricaria inodora* and *Veronica persica* when applied at a rate of 320 g/ha. At the same application rate, these compounds cause no damage whatsoever in maize.

2. Post-emergence Herbicidal Action Against Weed Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The inventive compounds formulated in the form of wettable powders (WP) or as emulsion concentrates (EC) are then sprayed onto the green parts of the plants as an aqueous suspension or emulsion at a water application rate of 600 to 800 l/ha (converted) with addition of 0.2% wetting agent. After the test plants have been left to stand in the greenhouse under optimal growth conditions for about 3 weeks, the action of the formulations is assessed visually in comparison to untreated controls (herbicidal action in percent (%): 100% activity=the plants have died, 0% activity=like control plants). Here, for example, compounds No. 1-1, 1-19, 1-20, 1-25, 1-34, 1-44, 1-61, 1-62, 1-68, 1-77, 1-78, 1-79, 1-119, 1-121, 1-123, 2-1, 2-34, 2-44, 2-62, 2-61, 2-62, 2-68, 2-103, 2-104, 2-105, 2-120 and 2-123 have in each case an at least 80% activity against *Abutilon theophrasti* and *Stellaria media* when applied at a rate of 80 g/ha.

We claim:

1. 4-Nitro-substituted N-(tetrazol-5-yl)-, N-(triazol-5-yl)- and N-(1,3,4-oxadiazol-2-yl)arylcarboxamides of formula (I) and/or a salt thereof

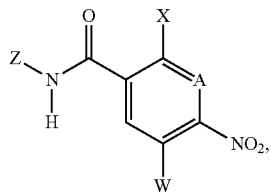

wherein
Z is $Z^1$ or $Z^2$ $Z^1$:

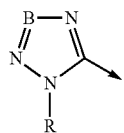

$Z^2$:

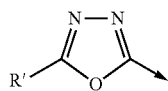

A is CY,
B is N or CH,
X is nitro, halogen, cyano, methyl, ethyl, n-propyl, isopropyl, trifluoromethyl, difluoromethyl, pentafluoroethyl, cyclopropyl, cyclopropylmethyloxy, methoxy, ethoxy, methylsulfanyl, methylsulfinyl, methylsulfonyl, methoxymethyl, ethoxymethyl, 2-methoxyethoxymethyl, methylsulfanylmethyl, methylsulfinylmethyl or methylsulfonylmethyl,
Y is nitro, halogen, cyano, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-cycloalkyl, $(C_3-C_6)$-cycloalkyl-$(C_1-C_6)$-alkyl, $R^1(O)C$, $R^1O(O)C$, $R^1O$, $R^2(O)_nS$, $R^1O$—$(C_1-C_6)$-alkyl, NC—$(C_1-C_6)$-alkyl, $(R^1)_2N$, heteroaryl-$(C_1-C_6)$-alkyl, heterocyclyl-$(C_1-C_6)$-alkyl, heteroaryl or heterocyclyl, where the last four radicals are substituted in each case by s radicals from the group halogen, nitro, cyano, methyl, trifluoromethyl, methoxy and methylsulfonyl, and where heterocyclyl bears n oxo groups,
W is hydrogen, chlorine or methyl,
R' is methyl, ethyl, n-propyl or methoxymethyl,
R is methyl, ethyl, n-propyl, prop-2-en-1-yl, 2-methoxyethyl, 2-ethoxyethyl or 2-(2-methoxyethoxy)ethyl,
$R^1$ is hydrogen, methyl, ethyl, n-propyl, isopropyl, prop-2-enyl, prop-2-inyl, trifluoromethyl, difluoromethyl, fluoromethyl, 2,2,2-trifluoroethyl, 2,2-difluoroethyl, 2-fluoroethyl, 2-chloroethyl, cyclopropyl, 2-methoxyethyl, 2-ethoxyethyl, 3-methoxypropyl, 3-ethoxypropyl, cyclopropylmethyl, 2-(trifluoromethoxy)ethyl, 3-(trifluoromethoxy)propyl, 2-(trifluoromethylsulfanyl)ethyl, 2-(trifluoromethylsulfynyl)ethyl, 2-(trifluoromethylsulfonyl)ethyl, 3-(trifluoromethylsulfanyl)propyl, 3-(trifluoromethylsulfinyl)propyl, 3-(trifluoromethylsulfonyl)propyl, N,N-dimethylaminocarbonylmethyl, 3-(1H-tetrazol-1-yl)propyl, 3-(1H-tetrazol-2-yl)propyl, tetrahydrofuran-2-yl-methyl, 1,4-dioxan-2-ylmethyl, 1,3-dioxolan-2-ylmethyl, or 2-methylsulfonylaminoethyl $R^2$ is methyl, ethyl, n-propyl, isopropyl, prop-2-enyl, prop-2-inyl, trifluoromethyl, difluoromethyl, fluoromethyl, 2,2,2-trifluoroethyl, 2,2-difluoroethyl, 2-fluoroethyl, 2-chloroethyl, cyclopropyl, 2-methoxyethyl, 2-ethoxyethyl, 3-methoxypropyl, 3-ethoxypropyl, cyclopropylmethyl, 2-(trifluoromethoxy)ethyl, 3-(trifluoromethoxy)propyl, 2-(trifluoromethylsulfanyl)ethyl, 2-(trifluoromethylsulfynyl)ethyl 2-(trifluoromethylsulfonyl)ethyl, 3-(trifluoromethylsulfanyl)propyl, 3-(trifluoromethyl-sulfinyl)propyl, 3-(trifluoromethylsulfonyl)propyl, N,N-dimethylaminocarbonylmethyl, 3-(1H-tetrazol-1-yl)propyl, 3-(1H-tetrazol-2-yl)propyl, tetrahydrofuran-2-yl-methyl, 1,4-dioxan-2-ylmethyl, 1,3-dioxolan-2-ylmethyl, or 2-methylsulfonylaminoethyl n is 0, 1 or 2,
s is 0, 1, 2 or 3.

2. N-(tetrazol-5-yl)-, N-(triazol-5-yl)- and N-(1,3,4-oxadiazol-2-yl)arylcarboxamide and/or a salt as claimed in claim 1, wherein
Z is $Z^1$
B is N.

3. N-(tetrazol-5-yl)-, N-(triazol-5-yl)- and N-(1,3,4-oxadiazol-2-yl)arylcarboxamide and/or a salt as claimed in claim 1, wherein
Z is $Z^2$.

4. A herbicidal composition comprising a herbicidally active content of at least one compound of formula (I) and/or a salt thereof as claimed in claim 1.

5. The herbicidal composition as claimed in claim 4 in a mixture with one or more formulation auxiliaries.

6. The herbicidal composition as claimed in claim 4, comprising at least one further pesticidally active substance selected from the group consisting of insecticides, acaricides, herbicides, fungicides, safeners and growth regulators.

7. The herbicidal composition as claimed in claim 6, comprising a safener.

8. The herbicidal composition as claimed in claim 7, comprising cyprosulfamide, cloquintocet-mexyl, mefenpyr-diethyl or isoxadifen-ethyl.

9. The herbicidal composition as claimed in claim 6, comprising a further herbicide.

10. A method for controlling unwanted plants, comprising applying an effective amount of at least one compound of formula (I) and/or salt as claimed in claim 1 to the plants and/or to a site of unwanted vegetation.

11. A compound of formula (I) and/or salt as claimed in claim 1 capable of being used for controlling one or more unwanted plants.

12. The method as claimed in claim 10, wherein said controlling is of unwanted plants in one or more crops of useful plants.

13. The method as claimed in claim 12, wherein the useful plants are transgenic useful plants.

14. N-(tetrazol-5-yl)-, N-(triazol-5-yl)- and N-(1,3,4-oxadiazol-2-yl)arylcarboxamide and/or a salt as claimed in claim 1, wherein Z is $Z^1$.

15. N-(tetrazol-5-yl)-, N-(triazol-5-yl)- and N-(1,3,4-oxadiazol-2-yl)arylcarboxamide and/or a salt as claimed in claim 3, wherein
R' is methoxymethyl.

16. N-(tetrazol-5-yl)-, N-(triazol-5-yl)- and N-(1,3,4-oxadiazol-2-yl)arylcarboxamide and/or a salt of formula I

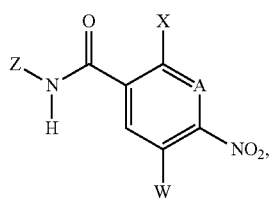

(I)

in which
Z is $Z^1$ or $Z^2$ $Z^1$:

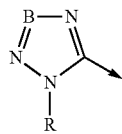

$Z^2$:

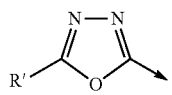

A is N,
B is N or CH,
X is nitro, halogen, cyano, formyl, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $R^1(O)C$, $R^1(R^1ON=)C$, $R^1O(O)C$, $(R^1)_2N(O)C$, $R^1O(R^1)N(O)C$, $R^1O$, $R^1(O)CO$, $(R^1)_2N(O)CO$, $R^2(O)_2SO$, $R^1O(O)CO$, $R^2(O)_nS$, $R^1O(O)_2S$, $(R^1)_2N(O)_2S$, $R^1(R^2)N$, $(R^1)_2N(O)C(R^1)N$, $R^1O(O)C(R^1)N$, $R^2(O)_2S(R^1)N$, $R^1(O)C(R^1)N$, $(R^5O)_2(O)P$, $(R^5O)_2(O)P$—$(C_1-C_6)$-alkyl, $R^2(O)_nS$—$(C_1-C_6)$-alkyl, $R^1O$—$(C_1-C_6)$-alkyl, $R^1(O)CO$—$(C_1-C_6)$-alkyl, $R^2(O)_2SO$—$(C_1-C_6)$-alkyl, $R^1O(O)C$—$(C_1-C_6)$-alkyl, $R^1O(O)_2S$—$(C_1-C_6)$-alkyl, $(R^1)_2N(O)C$—$(C_1-C_6)$-alkyl, $(R^1)_2N(O)_2S$—$(C_1-C_6)$-alkyl, $R^1(O)C(R^1)N$—$(C_1-C_6)$-alkyl, $R^2(O)_2S(R^1)N$—$(C_1-C_6)$-alkyl, heteroaryl-$(C_1-C_6)$-alkyl or heterocyclyl-$(C_1-C_6)$-alkyl, where the two last-mentioned radicals are substituted in each case by s radicals from the group consisting of halogen, nitro, cyano, thiocyanato $(C_1-C_6)$-alkyl, $(C_1-C_6)$-haloalkyl, $(C_3-C_6)$-cycloalkyl, $(C_1-C_6)$-alkyl-$(O)_nS$, $(C_1-C_6)$-alkoxy and $(C_1-C_6)$-haloalkoxy, and where heterocyclyl bears n oxo groups,
R is $(C_1-C_8)$-alkyl, $(C_1-C_8)$-haloalkyl, $(C_2-C_8)$-alkenyl, $(C_2-C_8)$-haloalkenyl or $(C_2-C_8)$-alkynyl, $(C_3-C_8)$-haloalkynyl, where these six abovementioned radicals are substituted in each case by s radicals from the group consisting of hydroxy, nitro, cyano, $(R^5)_3Si$, $(R^5O)_2(O)P$, $(C_1-C_6)$-alkyl-$(O)_nS$, $(C_1-C_6)$-haloalkyl-$(O)_nS$, $(C_1-C_6)$-alkoxy,$(C_1-C_6)$-haloalkoxy, $(R^3)_2N$, $R^3(O)C$, $R^3O(O)C$, $R^3(O)CO$, $R^3(O)C(R^3)N$, $R^4(O)_2S(R^3)N$, $(C_3-C_6)$-cycloalkyl-$(C_1-C_2)$-alkoxy, $(C_3-C_6)$-cycloalkyl, heteroaryl, heterocyclyl, phenyl, heteroaryl-Q, heterocyclyl-Q, phenyl-Q and benzyl-Q, where the eight last-mentioned radicals are substituted in each case by s radicals from the group consisting of methyl, ethyl, methoxy, trifluoromethyl, cyano and halogen, and where heterocyclyl bears n oxo groups, or
R is $(C_3-C_7)$-cycloalkyl, heteroaryl, heterocyclyl or phenyl, in each case substituted by s radicals from the group consisting of halogen, nitro, cyano, $(C_1-C_6)$-alkyl, $(C_1-C_6)$-haloalkyl, $(C_3-C_6)$-cycloalkyl, $(C_1-C_6)$-alkyl-$(O)_nS$, $(C_1-C_6)$-alkoxy, $(C_1-C_6)$-haloalkoxy and $(C_1-C_6)$-alkoxy-$(C_1-C_4)$-alkyl, where heterocyclyl bears n oxo groups,
Q is O, S or $(R^3)N$,
$R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkoxy-$(C_1-C_6)$-alkyl, $(C_3-C_6)$-cycloalkyl-$(C_1-C_6)$-alkyl, phenyl, phenyl-$(C_1-C_6)$-alkyl, heteroaryl, heteroaryl-$(C_1-C_6)$-alkyl, heterocycl, heterocyclyl-$(C_1-C_6)$-alkyl, heteroaryl-O—$(C_1-C_6)$-alkyl, heterocyclyl-O—$(C_1-C_6)$-alkyl, heteroaryl-$(R^3)N$—$(C_1-C_6)$-alkyl or heterocyclyl-$(R^3)N$—$(C_1-C_6)$-alkyl, where the 21 last-mentioned radicals are substituted in each case by s radicals from the group consisting of cyano, halogen, nitro, thiocyanato, $R^3O$, $R^4(O)_nS$, $(R^3)_2N$, $R^3O(R^3)N$, $R^3(O)C$, $R^3(O)CO$, $R^4(O)CS$, $R^3(O)C(R^3)N$, $R^4(O)_2S(R^3)N$, $R^3(O)_2C$, $R^4S(O)C$, $(R^3)_2N(O)C$ and $(C_1-C_4)$-alkoxy-$(C_2-C_6)$-alkoxycarbonyl, and where heterocyclyl bears n oxo groups,
$R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkoxy-$(C_1-C_6)$-alkyl, $(C_3-C_6)$-cycloalkyl-$(C_1-C_6)$-alkyl, phenyl, phenyl-$(C_1-C_6)$-alkyl, heteroaryl, heteroaryl-$(C_1-C_6)$-alkyl, heterocycl, heterocyclyl-$(C_1-C_6)$-alkyl, heteroaryl-O—$(C_1-C_6)$-alkyl, heterocyclyl-O—$(C_1-C_6)$-alkyl, heteroaryl-$(R^3)N$—$(C_1-C_6)$-alkyl or heterocyclyl-$(R^3)N$—$(C_1-C_6)$-alkyl, where the 21 last-mentioned radicals are substituted in each case by s radicals from the group consisting of cyano, halogen, nitro, thiocyanato, $R^3O$, $R^4(O)_nS$, $(R^3)_2N$, $R^3O(R^3)N$, $R^3(O)C$, $R^3(O)CO$, $R^4(O)CS$, $R^3(O)C(R^3)N$, $R^4(O)_2S(R^3)N$, $R^3(O)_2C$, $R^4S(O)C$, $(R^3)_2N(O)C$ and $(C_1-C_4)$-alkoxy-$(C_2-C_6)$-alkoxycarbonyl, and where heterocyclyl bears n oxo groups,
$R^3$ is hydrogen, $(C_1-C_6)$-alkyl, $(C_1-C_6)$-haloalkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl,
$R^4$ is $(C_1-C_6)$-alkyl, $(C_1-C_6)$-haloalkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl,
$R^5$ is $(C_1-C_4)$-alkyl,
$R^6$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl or is heteroaryl, heterocyclyl, in each case substituted by s radicals from the group methyl, ethyl, methoxy, trifluoromethyl and halogen, n is 0, 1 or 2, s is 0, 1, 2 or 3.

* * * * *